United States Patent
Sugihara et al.

(10) Patent No.: US 9,487,566 B2
(45) Date of Patent: Nov. 8, 2016

(54) METHOD FOR PURIFYING PROTEIN

(75) Inventors: Tsutomu Sugihara, Tokyo (JP); Tomoko Isoda, Tokyo (JP); Yuya Taniguchi, Tokyo (JP); Hidetaka Nomura, Tokyo (JP); Toshiyuki Suzawa, Tokyo (JP)

(73) Assignee: KYOWA HAKKO KIRIN CO., LTD, Tokyo (JP)

( * ) Notice: Subject to any disclaimer, the term of this patent is extended or adjusted under 35 U.S.C. 154(b) by 0 days.

(21) Appl. No.: 14/129,677

(22) PCT Filed: Jun. 28, 2012

(86) PCT No.: PCT/JP2012/066543
§ 371 (c)(1),
(2), (4) Date: Jan. 14, 2014

(87) PCT Pub. No.: WO2013/002330
PCT Pub. Date: Jan. 3, 2013

(65) Prior Publication Data
US 2014/0148585 A1    May 29, 2014

Related U.S. Application Data

(60) Provisional application No. 61/502,426, filed on Jun. 29, 2011.

(51) Int. Cl.
| C07K 1/18 | (2006.01) |
| C07K 14/47 | (2006.01) |
| C07K 14/81 | (2006.01) |
| C07K 1/16 | (2006.01) |

(52) U.S. Cl.
CPC ............ C07K 14/4703 (2013.01); C07K 1/165 (2013.01); C07K 1/18 (2013.01); C07K 14/8128 (2013.01)

(58) Field of Classification Search
None
See application file for complete search history.

(56) References Cited

U.S. PATENT DOCUMENTS

| 7,999,085 B2 * | 8/2011 | Gagnon ................. 530/415 |
| 2010/0113754 A1* | 5/2010 | Sugihara ............ C07K 14/8128 530/393 |
| 2010/0210821 A1* | 8/2010 | Gilljam et al. .............. 530/351 |

FOREIGN PATENT DOCUMENTS

| EP | 2311864 A1 | 4/2011 | |
| WO | WO86/07594 | * 12/1986 | .............. C07K 3/20 |
| WO | 2008/073620 A2 | 6/2008 | |
| WO | 2009/024620 A2 | 2/2009 | |
| WO | 2010/030222 A1 | 3/2010 | |

OTHER PUBLICATIONS

Egire et al. "Development and characterization of novel erythropoiesis stimulating protein (NESP)" Nephrol Dial Transplant 2001 16 [Suppl 3]:3-13.*
GE Healthcare/Life Sciences ("HiScreen™ Capto™ MMC Instructions", retrieved from the internet: <<https://www.gelifesciences.com/gehcls_images/GELS/Related%20Content/Files/1339074704082/litdoc28933956_20120607151746.pdf>>, retrieved on Jul. 28, 2015, first published on Feb. 2008).*
Kaleas K A et al., "Industrial case study: Evaluation of a mixed-mode resin for selective capture of a human growth factor recombinantly expressed in E. coil", Journal of Chromatography, Jan. 8, 2010, pp. 235-242, vol. 1217, No. 2, Elsevier Science Publishers B.V.
Extended European Search Report dated Oct. 13, 2014 issued by European Patent Office in counterpart European application No. 12804564.8.

* cited by examiner

Primary Examiner — Suzanne M Noakes
Assistant Examiner — Jae W Lee
(74) Attorney, Agent, or Firm — Sughrue Mion, PLLC

(57) ABSTRACT

The present invention relates to protein purification. More particularly, a method for directly recovering an objective protein from a protein composition and purifying a protein with a desired quality in a rapid and efficient manner is provided. Further, a rapid purification method capable of efficiently removing impurities included in the protein composition is provided. Therefore, compared to the conventional purification methods, quality and yield of the protein can be remarkably improved.

5 Claims, 8 Drawing Sheets

METHOD FOR PURIFYING PROTEIN

TECHNICAL FIELD

The present invention relates to protein purification. More particularly, a method for directly recovering an objective protein from a protein composition and efficiently purifying a protein with a desired quality is provided.

BACKGROUND ART

Development of genetic recombination technologies has provided a variety of protein pharmaceuticals. In particular, numerous antibody and protein pharmaceuticals have been recently developed and commercialized. To prepare these protein pharmaceuticals in an industrial and economic manner and in a high purity has become a more important issue in biopharmaceutical industry.

Generally, these antibody or protein pharmaceuticals are produced by culturing recombinant cells into which a vector including an objective protein gene is inserted. The culture fluid includes impurities such as various medium components, cell by-products or the like, in addition to the objective protein. Thus, it is very difficult and challenging to perform isolation and purification to meet purity requirements for pharmaceuticals, and further combine the industrial-scale production and economic efficiency.

In the preparation method of the objective protein, the purification process is a very important process in increasing purity of the protein while maintaining its physiological functions. In general, the purification process is carried out by a combination of different modes of chromatography based on differences in charge, hydrophilicity or molecular size, and a manipulation such as alcohol fractionation, salting-out, filtration, concentration or dilution, and the like (Non-Patent Document 1).

Chromatography may be exemplified by affinity chromatography, cation exchange chromatography, anion exchange chromatography, hydroxyapatite chromatography, reversed-phase chromatography, hydrophobic interaction chromatography, size exclusion chromatography, mixed mode chromatography and the like. A combination thereof can be carried out to purify the objective protein with a desired purity. In affinity chromatography, a carrier, on which a substance having affinity for the objective protein such as antibody or heparin is immobilized, is used.

If the objective protein is an antibody, a carrier, on which a ligand (affinity substance) interacting with a specific region of the antibody such as Protein A or Protein G is immobilized, is used. Further, considering the interaction between the carrier or buffer used in these chromatographies and objective protein and impurities, two methods can be employed; a capture mode for adsorbing the objective protein onto the carrier and then eluting it, and a flow-through mode for adsorbing impurities onto the carrier and then passing the objective protein through the carrier.

In particular, if the objective protein is an antibody, it has been already established to purify an object with a desired purity by Protein A affinity chromatography and by combinations of one or more of the chromatographies described above, and this technology has been used as a platform purification method.

Meanwhile, if the objective protein is proteins other than antibodies, there is no standard method as the platform purification method of the protein with the desired purity. Considering the characteristics of the objective protein, a purification process is designed by repeating a test by trial and error respectively, and optimized for each objective protein respectively, and then practically applied.

Affinity chromatography using an antibody having an affinity for the objective protein has been also used for purification. However, there are many problems that a ligand (affinity substance) specific to the objective protein must be used, it is no always easy to obtain a ligand having a desired binding property or affinity, a carrier binding with the ligand is considerably expensive, and there is a concern for its stable supply. Therefore, it is not easy to achieve its industrial application.

Under this background, there is a need to establish a standard technology capable of purifying the objective protein in a simple, efficient, and rapid manner.

Meanwhile, when a simple chromatography other than affinity chromatography is used, pretreatment of cell culture supernatant or the like is essential for purification of the objective protein. Typically, the cell culture supernatant includes a large amount of cell metabolites or medium components, and components derived from additives during cultivation, and the cell culture supernatant has high conductivity or salt concentration in many cases.

In this regard, it is not efficient to directly load the culture supernatant to the chromatography, and thus a pretreatment such as several-fold dilution of the culture supernatant, exchange of a buffer, exchange of the buffer after concentration, dilution after concentration or the like are typically performed.

However, because such pretreatments require several hours to 1 day or longer of manipulation time, and depend on production facility such as size of dilution tank or the like, the production methods are not efficient and practical in terms of industrial application. Further, quality of the objective protein may deteriorate during pretreatment of the culture supernatant such as concentration or the like.

As such, the pretreatment manipulation becomes a challenging issue in the industrial production method of the protein with a high purity. There is a need for a purification method capable of efficiently recovering the objective protein by a simple pretreatment manipulation without damaging quality of the protein.

Further, in order to supply and use the objective protein as a medicine, it is required that the objective protein is highly purified from a composition such as culture fluid in order to have a desired biological activity. However, most of the compositions containing the objective protein as a starting point of purification, like culture fluid, include trace elements having a proteolytic activity or impurities. If these components are not inactivated or removed, there are concerns for damage in the biological activity of the objective protein, a reduction in the yield, modification, production of by-products, or the like. In addition, the impurities are concentrated or activated during the above described pretreatment of the culture supernatant, which may deteriorate the objective protein.

The components or impurities may be exemplified by glycolytic enzymes, proteolytic enzymes, oxidoreductases and the like which are retained within the producing cells. Examples of the glycolytic enzymes may include neuraminidase (sialidase), galactosidase, glycanase and the like.

Examples of the proteolytic enzymes may include serine protease, esterase, cysteine protease, trypsin-like protease, aminopeptidase, aspartic protease, cathepsin and the like.

Examples of the oxidoreductases may include thioredoxin or the like involved in a cascade reaction. Amino acid isomerase such as transglutaminase or the like is also known as an enzyme modifying protein structures.

For example, rapid separation of neuraminidase from a mixture solution of glycoprotein and neuraminidase can be performed in combinations of alcohol fractionation, salting-out, ion-exchange chromatography, hydrophobic interaction chromatography, gel filtration chromatography, or affinity chromatography described above, but stable purification method of the objective protein by using only these methods is extremely limited.

It can be also considered that an enzyme inhibitor (divalent cations such as copper, sialic acid and derivatives thereof, sialyllactose, oligosialic acid, polysialic acid, Tamiflu, BCX-1812, sialidase neutralizing antibody, or the like.) is used to inhibit the enzymatic activity of neuraminidase for purification. However, it is not convenient to use a large amount of these inhibitors in the preparation process, and during purification process, there is a limitation in removing them to a concentration with no toxicity.

As such, many compositions such as a culture fluid containing the objective protein or the like include a plurality of impurities that damage the structure or stability of protein as trace elements. In order to obtain the protein with the desired quality, these impurities are required to be removed in a safe, rapid and efficient manner.

Further, the objective protein degraded or modified by the above described impurities or the objective protein biologically inactivated itself can be also impurities. In the case of glycoproteins containing sugar chains, the sugar chains are known to be greatly involved in physiological activity, stability, in vivo kinetics, solubility or the like.

When glycoproteins are produced using animal cells that are prepared by application of genetic recombination technique, neuraminidase released from dead cells are included in the obtained culture fluid. Therefore, sialic acid is removed from sugar chains of the objective glycoproteins. When sialic acid is eliminated from the glycoprotein, the galactose residue exposed to the non-reducing-end is captured by an asialoglycoprotein receptor (galactose receptor) localized in the liver and quickly degraded (Non-Patent Document 2).

As such, when the number of sialic acids bound at the terminal sugar chain is low, the blood half-life of glycoproteins is reduced, and their physiological activities cannot be sufficiently exerted. It has been also known that biological activity of Erythropoietin or the like depends on the number of sialic acids bound to the sugar chain.

Thus, because glycoproteins in which sialic acids are eliminated or glycoproteins in which the number of bound sialic acids is degradated may become impurities, it is necessary to remove neuraminidase in order to prevent elimination of sialic acid or to remove proteins having a lower number of bound sialic acids, as described above.

It is very difficult and challenging to control the composition or content of the sugar chains of proteins by chromatography. Thus, there is a demand to develop a method for purifying glycoproteins in a high purity while maintaining their sugar chains in the desired quality.

In another case, the objective protein denatured during the preparation process can be also impurities in itself. For example, aggregates (or associates, aggregates, dimers, oligomers, aggregates, multimers) resulting from denaturation of the objective proteins during the preparation process are problematic in terms of reduction of biological activity, change in in vivo kinetics, antigenicity or the like.

For example, in the case of Protein S, generation of aggregates cannot be inhibited by the typical purification method, and a purification method of generating no aggregates has not been known yet (Non-Patent Document 3).

Further, a purification method for efficiently reducing the content of a cleaved form (a nicked form) has not been developed. For this reason, it is required to establish a purification method capable of removing impurities derived from the objective protein, such as aggregates or cleaved forms, in order to a sufficiently low level during purification process.

Under this background, there is a need for a method for easily purifying a protein with a desired quality by removing impurities related to the protein quality.

Meanwhile, various modes of chromatography carriers has been developed as a technology for purifying the objective protein from the protein composition in a high purity. Of them, a mixed mode carrier (or multimode carrier) is a chromatography carrier prepared by immobilizing ligands of mode of having two or more characteristics onto a single carrier, which has been recently developed.

The mixed mode carrier is known to have a unique separation property as well as that of combined two modes, and has been a useful tool for protein purification (Non-Patent Document 4).

However, there has been no report on a standard method for purifying other proteins, except for antibodies, using the mixed mode carrier. The mixed mode carrier such as Capto adhere (manufactured by GE Healthcare) having an anion exchange group and a hydrophobic interaction group, is known only as a subsequent purification following a rough purification process of the antibody composition using Protein A chromatography, or the like (Patent Documents 1 to 3 and Non-Patent Document 5).

In this case, impurities to be removed are mainly host cell-derived proteins (HCP) or DNA, and quality of the objective protein itself cannot be changed or the ingredients thereof cannot be controlled (Non-Patent Documents 6 and 7).

Further, the mixed mode carrier such as Capto MMC (manufactured by GE Healthcare) having a cation exchange group and a hydrophobic interaction group, is known as a method for recovering the objective protein from a high-salt composition (Non-Patent Documents 8 to 9), and is also used in antibody purification (Patent Document 4). However, there are many limitations in the use in the first purification step for removing impurities related to the protein quality, controlling the ingredient, and obtaining the protein with the desired quality.

In particular, there is no report on a method for directly recovering and controlling sialic acids binding to sugar chains of proteins, aggregates or fragments of the protein itself by the first chromatography. Further, there are no reports on a method for purifying acidic proteins using a mixed mode carrier having a cation exchange group and a method for purifying basic proteins using a mixed mode carrier having an anion exchange group.

CITATION LIST

Patent Documents

[Patent Document 1] International Publication WO 2010/071208
[Patent Document 2] International Publication WO 2010/030222
[Patent Document 3] International Publication WO 2006/043895
[Patent Document 4] International Publication WO 2009/126603

Non-Patent Documents

[Non-Patent Document 1] Robert K. Scopes, Protein Purification Principles and Practice, Third Edition, 1994, Springer-Verlag New York, Inc.

[Non-Patent Document 2] Metabolism, 1983, 20, 153.

[Non-Patent Document 3] Kristin M. Sere, George M. Willems, Jan Rosing, Tilman M. Hackeng, Protein S multimers are generated in vitro and affect Protein S structure-function analysis, 2006, Seminars in Hematology 43 (suppl 1) S111-S120.

[Non-Patent Document 4] Kennedy, L. A., Kopaciewicz, W., Regnier, F. E., Multimodal liquid chromatography columns for the separation of proteins in either the anion-exchange or hydrophobic-interaction mode, 1986, Journal of Chromatography A, Vol. 359, 73-84.

[Non-Patent Document 5] Chen J., Tetrault J., Zhang Y., Wasserman A., Conley G, DiLeo M., Haimes E., Ley A., The distinctive separation attributes of mixed-mode resins and their application in monoclonal antibody downstream purification process, 2010 J. Chromatogr. A 1217(2), 216-224.

[Non-Patent Document 6] GE Healthcare Capto Adhere Data File 71-2779-11, http://www.gelifesciences.co.jp/catalog/pdf/Capto_adhere.pdf

[Non-Patent Document 7] Eriksson K., Ljunglof A., Rodrigo G., Brekkan E., Mab contaminant removal with a multi-modal anion exchanger: A platform step to follow Protein A, 2009, BioProcess international 7(2), 52-56.

[Non-Patent Document 8] GE Healthcare Capto MMC Date File 11-0035-45AA, http://www.gelifesciences.co.jp/catalog/pdf/11003545aa.pdf

[Non-Patent Document 9] BioPharm International May, 11, 2011

SUMMARY OF THE INVENTION

Problems to be Solved by the Invention

A simple method for directly recovering an objective protein from a protein composition and purifying the protein with a desired quality in a rapid and efficient manner is needed in the industrial-scale production of proteins.

Means for Solving the Problems

The present inventors have made many efforts to solve the above problems. Surprisingly, they found that objective protein can be purified with a desired quality in a rapid and efficient manner by proper combinations of using a mixed mode carrier in a first purification step, controlling separation conditions, washing and/or eluting using a buffer containing amino acids, and selecting elution fractions, thereby completing the present invention.

The present invention relates to (1) to (29) below.

(1) A method for purifying a protein, comprising a first chromatographic process including one or more of the following processes of (a) to (d):

(a) a process of directly contacting a protein composition with a mixed mode carrier;

(b) a process of washing and/or eluting the mixed mode carrier using a buffer weakening affinity of impurities for the mixed mode carrier so as to remove impurities;

(c) a process of washing and/or eluting the mixed mode carrier using a buffer containing an amino acid so as to remove impurities;

(d) a process of obtaining only a fraction of the purified protein with a desired quality.

(2) The purification method described in (1), wherein the mixed mode carrier has an ion exchange group and a hydrophobic interaction group.

(3) The purification method described in (1) or (2), wherein the mixed mode carrier is selected from Capto adhere, Capto MMC, HEA HyperCel, PPA HyperCel, MEP HyperCel, or TOYOPEARL MX-Trp-650M.

(4) A method for purifying a protein, comprising a first chromatographic process including one or more of the following processes of (a) to (c):

(a) a process of contacting a protein composition with an anion exchange carrier;

(b) a process of washing and/or eluting the anion exchange carrier using a buffer weakening affinity of impurities for the anion exchange carrier so as to remove impurities; and (c) a process of washing and/or eluting the anion exchange carrier using a buffer containing an amino acid so as to remove impurities.

(5) The purification method described in any one of (1) to (4), wherein a recovery of the purified protein is 50% or more.

(6) The purification method described in any one of (1) to (5), wherein the protein is a glycoprotein.

(7) The purification method described in (6), wherein the glycoprotein is a glycoprotein containing a sialic acid-bound sugar chain.

(8) The purification method described in (7), wherein the glycoprotein containing a sialic acid-bound sugar chain is Antithrombin, Protein SErythropoietin, or derivatives thereof.

(9) The purification method described in (7) or (8), wherein the number of bound sialic acids of the purified glycoprotein is 70% or more of the maximum number to be added.

(10) The purification method described in any one of (1) to (9), further comprising one or more chromatographic processes after the first chromatographic process.

(11) The purification method described in any one of (1) to (10), wherein the further chromatographic process is a chromatography using any one of a mixed mode carrier, an anion exchange carrier, an anion exchange membrane, a cation exchange carrier, a cation exchange membrane, a hydrophobic interaction carrier, a size exclusion carrier, a gel filtration carrier, a reversed-phase carrier, a hydroxyapatite carrier, a fluorapatite carrier, a sulfated cellulose carrier, or a sulfated agarose carrier.

(12) A composition comprising a protein that is purified by the method described in any one of (1) to (11).

(13) A method for purifying Antithrombin, comprising a first chromatographic process including one or more of the following processes of (a) to (d):

(a) a process of directly contacting an Antithrombin composition with a mixed mode carrier;

(b) a process of washing and/or eluting the mixed mode carrier using a buffer weakening affinity of impurities for the mixed mode carrier so as to remove impurities;

(c) a process of washing and/or eluting the mixed mode carrier using a buffer containing an amino acid so as to remove impurities;

(d) a process of obtaining only a fraction of Antithrombin with a desired quality.

(14) The purification method described in (13), wherein the number of bound sialic acids of the purified Antithrombin is 70% or more of the maximum number to be added.

(15) A method for purifying Antithrombin, comprising a first chromatographic process including one or more of the following processes of (a) to (d):
   (a) a process of contacting an Antithrombin composition with an anion exchange carrier;
   (b) a process of washing and/or eluting the anion exchange carrier using a buffer weakening affinity of impurities for the anion exchange carrier so as to remove impurities;
   (c) a process of washing and/or eluting the anion exchange carrier using a buffer containing an amino acid so as to remove impurities;
   (d) a process of obtaining only a fraction of Antithrombin with a desired quality.
(16) The purification method described in (15), wherein the number of bound sialic acids of the purified Antithrombin is 70% or more of the maximum number to be added.
(17) A method for purifying Protein S, comprising a first chromatographic process including one or more of the following processes of (a) to (d):
   (a) a process of directly contacting a Protein S composition with a mixed mode carrier;
   (b) a process of washing and/or eluting the mixed mode carrier using a buffer weakening affinity of impurities for the mixed mode carrier so as to remove impurities;
   (c) a process of washing and/or eluting the mixed mode carrier using a buffer containing an amino acid so as to remove impurities;
   (d) a process of obtaining only a fraction of Protein S with a desired quality.
(18) A method for purifying a protein, comprising a first chromatographic process including the following processes of (a) to (d):
   (a) a process of directly contacting a protein composition with a mixed mode carrier;
   (b) a process of washing and/or eluting the mixed mode carrier using a buffer weakening affinity of impurities for the mixed mode carrier so as to remove impurities;
   (c) a process of washing and/or eluting the mixed mode carrier using a buffer containing an amino acid so as to remove impurities;
   (d) a process of obtaining only a fraction of the purified protein with a desired quality.
(19) A method for purifying a protein, comprising a chromatographic process wherein the purified protein with a desired quality is obtained in a first chromatographic process including one or more of the following processes of (a) to (d):
   (a) a process of directly contacting a protein composition with a mixed mode carrier;
   (b) a process of washing and/or eluting the mixed mode carrier using a buffer weakening affinity of impurities for the mixed mode carrier so as to remove impurities;
   (c) a process of washing and/or eluting the mixed mode carrier using a buffer containing an amino acid so as to remove impurities;
   (d) a process of obtaining only a fraction of the purified protein with a desired quality.
(20) A method for purifying a protein, comprising a first chromatographic process including two or more of the following processes of (a) to (d):
   (a) a process of directly contacting a protein composition with a mixed mode carrier;
   (b) a process of washing and/or eluting the mixed mode carrier using a buffer weakening affinity of impurities for the mixed mode carrier so as to remove impurities;
   (c) a process of washing and/or eluting the mixed mode carrier using a buffer containing an amino acid so as to remove impurities;
   (d) a process of obtaining only a fraction of the purified protein with a desired quality.
(21) A method for purifying a protein, comprising a first chromatographic process including three or more of the following processes of (a) to (d):
   (a) a process of directly contacting a protein composition with a mixed mode carrier;
   (b) a process of washing and/or eluting the mixed mode carrier using a buffer weakening affinity of impurities for the mixed mode carrier so as to remove impurities;
   (c) a process of washing and/or eluting the mixed mode carrier using a buffer containing an amino acid so as to remove impurities;
   (d) a process of obtaining only a fraction of the purified protein with a desired quality.
(22) A method for purifying a protein, comprising a first chromatographic process including at least the following processes of (a) and (b):
   (a) a process of directly contacting a protein composition with a mixed mode carrier;
   (b) a process of washing and/or eluting the mixed mode carrier using a buffer weakening affinity of impurities for the mixed mode carrier so as to remove impurities;
(23) A method for purifying a protein, comprising a first chromatographic process including at least the following processes of (a) to (c):
   (a) a process of directly contacting a protein composition with a mixed mode carrier;
   (b) a process of washing and/or eluting the mixed mode carrier using a buffer weakening affinity of impurities for the mixed mode carrier so as to remove impurities;
   (c) a process of washing and/or eluting the mixed mode carrier using a buffer containing an amino acid so as to remove impurities;
(24) A method for purifying a protein, comprising a first chromatographic process including the following processes of (a) to (d):
   (a) a process of directly contacting a protein composition with an anion exchange carrier;
   (b) a process of washing and/or eluting the anion exchange carrier using a buffer weakening affinity of impurities for the anion exchange carrier so as to remove impurities;
   (c) a process of washing and/or eluting the anion exchange carrier using a buffer containing an amino acid so as to remove impurities;
   (d) a process of obtaining only a fraction of the purified protein with a desired quality.
(25) A method for purifying a protein, comprising a chromatographic process wherein the purified protein with a desired quality is obtained in a first chromatographic process including the following processes of (a) to (c):
   (a) a process of directly contacting a protein composition with an anion exchange carrier;
   (b) a process of washing and/or eluting the anion exchange carrier using a buffer weakening affinity of impurities for the anion exchange carrier so as to remove impurities;
   (c) a process of washing and/or eluting the anion exchange carrier using a buffer containing an amino acid so as to remove impurities;
(26) The purification method described in (19) or (25), wherein the desired quality is one or more of the followings:

(a) the number of bound sialic acids per protein is 70% or more of the maximum number to be added;

(b) the content of aggregate or cleaved form is 10% or less

(27) A method for purifying Antithrombin, comprising a first chromatographic process including at least the following processes of (a) to (d):

(a) a process of directly contacting an Antithrombin composition with a mixed mode carrier;

(b) a process of washing and/or eluting the mixed mode carrier using a buffer weakening affinity of impurities for the mixed mode carrier so as to remove impurities;

(c) a process of washing and/or eluting the using a buffer containing an amino acid so as to remove impurities;

(d) a process of obtaining only a fraction of Antithrombin with a desired quality.

(28) A method for purifying Antithrombin, comprising a first chromatographic process including at least the following processes of (a) to (d):

(a) a process of contacting an Antithrombin composition with an anion exchange carrier;

(b) a process of washing and/or eluting the anion exchange carrier using a buffer weakening affinity of impurities for the anion exchange carrier so as to remove impurities;

(c) a process of washing and/or eluting the anion exchange carrier using a buffer containing an amino acid so as to remove impurities;

(d) a process of obtaining only a fraction of Antithrombin with a desired quality.

(29) A method for purifying Protein S, comprising a first chromatographic process including at least the following processes of (a) to (d):

(a) a process of directly contacting a Protein S composition with a mixed mode carrier;

(b) a process of washing and/or eluting the mixed mode carrier using a buffer weakening affinity of impurities for the mixed mode carrier so as to remove impurities;

(c) a process of washing and/or eluting the mixed mode carrier using a buffer containing an amino acid so as to remove impurities;

(d) a process of obtaining only a fraction of Protein S with a desired quality.

Effect of the Invention

The present invention provides a technique of efficiently purifying the protein with a desired quality (hereinafter, referred to as "purified protein") by directly recovering an objective protein from a protein composition, and efficiently removing impurities related to the quality of the protein itself.

Specifically, a protein composition such as culture supernatant or the like is directly applied to a chromatography using a mixed mode carrier, thereby efficiently recovering the purified protein while maintaining its quality. Therefore, treatment or manipulation time before chromatography can be reduced, and deterioration in the quality of the objective protein can be also prevented during pretreatment of the culture supernatant such as concentration or the like.

Further, provided is a rapid purification method capable of efficiently removing impurities included in the protein composition. Therefore, compared to the conventional purification methods, quality and yield of the protein can be remarkably improved.

More specifically, provided is a method for preparing purification products of glycoproteins such as Antithrombin, Erythropoietin, Protein S, or derivatives thereof having the desired number of bound sialic acids, the desired content of aggregates or fragments in a yield applicable to practical preparation.

The protein prepared by the present invention is useful as a medicine.

EMBODIMENTS FOR CARRYING OUT THE INVENTION

Figure 1:
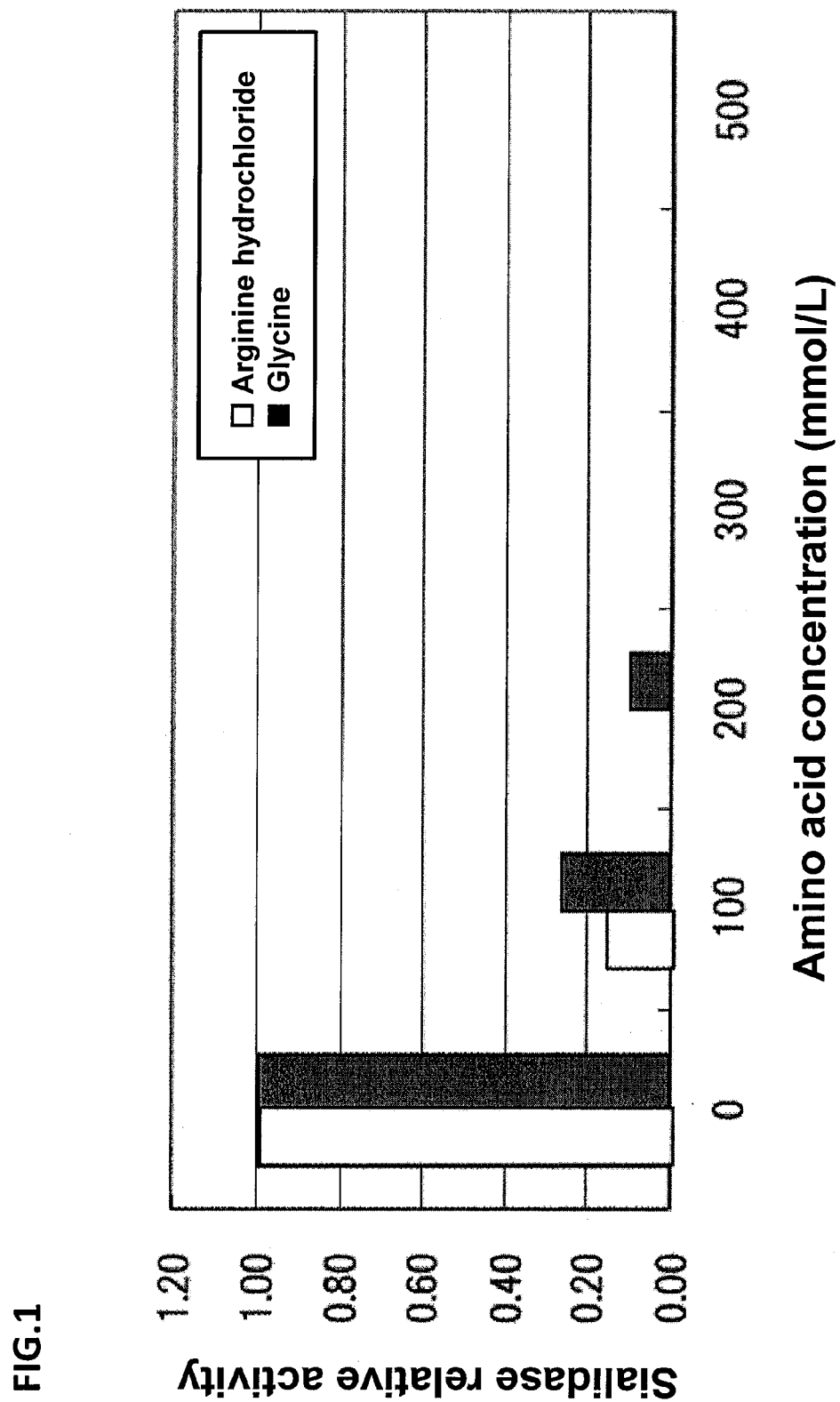
FIG. 1 shows the level of neuraminidase activity inhibited by addition of amino acids.

The present invention relates to a method for purifying a protein, including a first chromatographic process including at least one of the following processes of (a) to (d):

(a) a process of directly contacting a protein composition with a mixed mode carrier;

(b) a process of washing and/or eluting the mixed mode carrier using a buffer weakening affinity of impurities for the mixed mode carrier so as to remove impurities;

(c) a process of washing and/or eluting the mixed mode carrier using a buffer containing amino acids so as to remove impurities;

(d) a process of obtaining only a fraction of the purified protein with a desired quality.

The present invention relates to a purification method for obtaining the purified protein with the desired quality by proper combinations of directly contacting a protein composition such as culture supernatant or the like with the mixed mode carrier, rapidly separating or reducing components producing objective protein-derived impurities or the objective protein-derived impurities themselves from the protein composition, using a buffer containing amino acids, and selecting an elution fraction.

As used herein, the phrase "directly contacting with the mixed mode carrier" means not conducting several-fold dilution of the protein composition such as culture supernatant or the like, exchange of the buffer, exchange of the buffer after concentration, or dilution after concentration.

In the present invention, the protein composition may be any one, as long as it is an aqueous solution containing the objective protein. In the present invention, the protein may be exemplified by natural or non-natural proteins having no sugar chains, natural or non-natural glycoproteins, derivatives thereof, or the like.

Specific examples thereof may include Erythropoietins, darbepoetins, Antithrombins (α or β form, or a mixture thereof), interferons, interleukins, Protein S, tissue plasminogen activator, Factor VII, VIII, and IX, thrombomodulins, glucocerebrosidase, α-galactosidase, α-L-iduronidase, acidic α-glucosidase, Granulocyte-Colony Stimulating Factor (G-CSF), Granulocyte Macrophage-Colony Stimulating Factor (GM-CSF), Thrombopoietin or Megakaryocyte Growth and Development Factor (MGDF), Fibroblast Growth Factor (FGF), Epidermal Growth Factor (EGF), Insulin-like Growth Factor, Brain-Derived Neurotrophic Factor (BDNF), Ciliary Neurotrophic Factor (CNTF), Glial cell line-Derived Neurotrophic Factor (GDNF), antibodies and derivatives thereof, or the like.

These proteins are prepared from a composition that is obtained from the living body such as plasma, urine or the like, a culture fluid of cells or bacteria that is obtained by using a genetic recombination technique or a cell fusion technique, a composition that is obtained from transgenic non-human animal or plant, or the like, as a starting raw material.

The protein-producing cells may be exemplified by transgenic cells having an objective protein-encoding gene integrated thereto. Specific examples thereof may include cell lines such as animal cells, plant cells, yeast cells or the like.

More specific examples thereof may include cells that are prepared by introducing the protein gene into Chinese hamster ovary cells (CHO cell), mouse myeloma cells such as NS0 cells or SP2/0 cells, rat myeloma cells such as YB2/0 cells, IR983F cells, Syrian hamster kidney-derived cells such as BHK cells, human myeloma cells such as Namalwa cell, embryo-stem cell, amphicytula or the like.

The medium for culturing the protein-producing cells may be any one, as long as it is suitable for culturing each cell. Example of the medium for animal cell culture may include a basal medium typically used for animal cell culture. For example, any one of a medium containing serum, a medium containing no animal-derived component such as serum albumin or serum fraction, a serum-free medium, or a protein-free medium may be used, but the serum-free medium or the protein-free medium is preferably used.

The medium may be exemplified by RPMI1640 medium [The Journal of the American Medical Association, 199, 519 (1967)], Eagle's MEM medium [Science, 122, 501 (1952)], Dulbecco's modified MEM (DMEM) medium [Virology, 8, 396 (1959)], 199medium [Proceeding of the Society for the Biological Medicine, 73, 1 (1950)], F12 medium [Proc. Natl. Acad. Sci. USA, 53, 288 (1965)], Iscove's Modified Dulbecco's medium (IMDM medium) [J. Experimental Medicine, 147, 923 (1978)], EX-CELL302 medium, EX-CELL-CD-CHO medium, EX-CELL 325 medium (all manufactured by SAFC bioscience), CD-CHO medium, CD DG44 medium (all manufactured by Invitrogen) or IS CD- CHO medium (manufactured by Irvine Scientific), or modified media thereof, mixed media thereof or concentrated media thereof. Among them, RPMI1640 medium, DMEM medium, F12 medium, IMDM medium, EX-CELL302 medium, CD-CHO medium or IS CD-CHO medium is preferred.

If necessary, physiologically active materials or nutrient factors essential for growth of the protein-producing cells may be also added. These additives are included in the medium prior to culture, or further supplied to the culture fluid as an additive medium or as an additive solution during culture. The supplying method may be in any form such as a single solution or a mixed solution of two or more, and the addition method may be any one of continuous and intermittent methods.

The transgenic non-human animal or plant producing the protein may be a non-human animal or plant having a gene encoding the protein that is inserted into the cell. Example of the non-human animal may include mouse, rat, guinea pig, hamster, rabbit, dog, sheep, pig, goat, cattle, monkey or the like. Example of the plant may include Indian weed, potato, tomato, carrot, soybean, brassica, alfalfa, rice, wheat, barley, corn or the like.

Examples of the method for producing the protein composition may include a method described in WO 2008/120801 for an Antithrombin composition, a method described in Japanese Patent publication NO. H3-198792 for an Erythropoietin composition, a method described in WO 2010/018847 for a Protein S composition, or the like.

If insoluble materials such as cells or particles are present in the "protein composition" thus produced, they are removed therefrom, and after the insoluble materials are removed, the protein composition is applied to the purification method of the present invention. The method for removing insoluble materials such as cells or particles may be performed by using any one selected from continuous centrifugation, batch-type centrifugation, depth filtration, microfiltration, activated carbon or the like, or in combinations thereof. If necessary, pH of the protein composition is adjusted, and then provided for the purification method.

In the present invention, the protein composition to be contacted with the mixed mode carrier as the first chromatography is not required to be pre-treated, except that insoluble materials are removed therefrom and pH thereof is adjusted. For example, it is not necessary to perform buffer exchange by cross flow filtration using an ultrafiltration membrane (tangential flow filtration) or dialysis. Also, a pretreatment such as dilution with water or buffer is not needed.

In the present invention, when the mixed mode carrier is used, a distinctive procedure for purifying the objective protein from the protein composition may be performed, for example, in this order: (1) a process of directly contacting the protein composition with the mixed mode carrier so as to adsorb the objective protein thereto, and (2) a process of controlling quality of the objective protein. The process of (2) is further divided into (2-1) a process of separating impurities so as to elute the objective protein and (2-2) a process of recovering a particular range of fractions of the eluate.

In the present invention, the mixed mode carrier used in chromatography is preferably a carrier prepared by immobilizing two or more kinds of functional groups having different selectivities, preferably an ion exchange group and a hydrophobic interaction group, onto a solid-phase matrix.

Examples of the ion exchange group may include cation exchange groups such as a sulfate group, a methyl sulfate group, a sulfophenyl group, a sulfopropyl group, a carboxymethyl group or the like, or anion exchange groups such as a quaternary ammonium group, a quaternary aminoethyl group, a diethylaminoethyl group, a diethylaminopropyl group or the like.

Examples of the hydrophobic interaction group may include a methyl group, an ethyl group, a propyl group, an isopropyl group, a butyl group, a tert-butyl group, an octyl group, an ether group, a phenyl group or the like.

In the present invention, examples of the solid-phase matrix may include polymers such as cellulose, sepharose, agarose, chitosan, acrylic acid polymers, styrene-divinylbenzene copolymers and derivatives thereof (including crosslinked polymers), silica particles, glass particles, ceramic particles, surface-treated particles thereof, or the like.

The functional group may be directly immobilized onto the solid-phase matrix or indirectly immobilized onto the solid-phase matrix as a polymer (graft chain) having a plurality of functional groups.

Specific examples of the mixed mode carrier may include Capto adhere, Capto MMC (all manufactured by GE Healthcare), HEA HyperCel, PPA HyperCel, MEP HyperCel (all manufactured by Pall Corp.), TOYOPEARL MX-Trp-650M (manufactured by TOSOH Corporation) or the like, but are not limited thereto.

The first process of the present invention, "process of directly contacting the protein composition with the mixed mode carrier to adsorb the objective protein thereto" is performed in a capture mode (adsorption mode). The above described protein composition is applied to a column packed with the mixed mode carrier so as to adsorb the objective protein onto the carrier.

The condition for adsorbing the protein onto the mixed mode carrier may be preferably pH 4 to 9, and more preferably pH 5 to 8. The adsorption amount of the protein per 1 mL of the carrier is preferably 1 to 50 mg, and more preferably 5 mg or more.

Conductivity is preferably 0.01 mS/cm to 50 mS/cm, and more preferably 0.1 to 20 mS/cm. The amount of the mixed mode carrier is determined such that preferably 50% or more, more preferably 70% or more, and much more preferably 80% or more of the objective protein included in the protein composition are adsorbed, and the protein is recovered in the process yield of preferably 50% or more, more preferably 70% or more, and much more preferably 80% or more.

In the first step of the second process of the present invention, "process of separating impurities and eluting the objective protein", impurities are removed or separated to a desired level until the objective protein is eluted from the mixed mode carrier. The first impurities to be removed or separated may include components generating the objective protein-derived impurities, that is, components changing the properties of the objective protein.

Specific examples thereof may include glycolytic enzymes, proteolytic enzymes, oxidoreductases or the like. Examples of the glycolytic enzymes may include neuraminidase (sialidase), galactosidase, glycanase or the like.

Examples of the proteolytic enzymes may include serine protease, esterase, cysteine protease, trypsin-like protease, aminopeptidase, aspartic protease, cathepsin or the like.

Examples of the oxidoreductases may include thioredoxin-related enzymes such as thioredoxin reductase or the like. Example of the amino acid isomerase may include transglutaminase or the like. These impurities may be mainly derived from the objective protein-producing host cells.

The second impurities to be removed or separated are mainly those derived from the objective protein, which are generated by the above described first impurities, and examples thereof may include modified proteins undergone degradation, denaturation, sugar-chain removal, oxidation or deamidation, aggregated proteins or the like.

This process may be performed by the following procedures. The objective protein is adsorbed onto the mixed mode carrier, and then washed with a buffer to wash and remove the impurities. The buffer conditions for washing impurities are selected from the preferred conditions under which impurities are not adsorbed while the objective protein are adsorbed, or affinity between the impurities and the carrier is reduced, by varying pH, conductivity, ingredients of the buffer, salt concentration, additive or the like. By selecting the conditions, differences in physicochemical properties between impurities and the objective protein, for example, differences in isoelectric point, charge, hydrophobicity, molecular size, conformation or the like may be employed.

These differences may occur by elimination of sialic acid from the objective protein, changes in charge, oxidation, changes in hydrophobicity or molecular size by aggregation or cleavage, denaturation depending on solution conditions, or the like.

Specific conditions of the buffer used for washing are selected from the conditions under which changes in affinity of impurities and the objective protein for the mixed mode carrier are generated, and preferably pH 4 to 9, and more preferably pH 5 to 8. Conductivity is preferably 0.01 to 300 mS/cm, and more preferably 0.1 to 250 mS/cm.

A proper pH at which a difference in affinity occurs can be selected from combinations of ion exchange group and hydrophobic interaction group in the mixed mode carrier, by those skilled in the art, but it can be determined with reference to isoelectric points of the objective protein and impurities.

For example, in Example 1 described later, both Antithrombin and neuraminidase are acidic proteins having isoelectric points at acidic pH. However, because neuraminidase has an isoelectric point more close to neutral pH, its pH at which the mixed mode carrier having an anion exchange group does not bind thereto is higher than such a pH of Antithrombin.

Therefore, proper pH generating a difference in affinity of both proteins can be selected by examining the binding of the objective protein and impurities while pH of the buffer is gradually increased (e.g., each 0.2 increase in pH) from the acidic condition (e.g., pH 6.0), at which both neuraminidase and Antithrombin are adsorbed onto the carrier, to pH around the isoelectric point of neuraminidase.

Further, a proper salt concentration generating a difference in affinity of both proteins can be selected by adding salt in order to change the hydrophobic interaction between neuraminidase and the mixed mode carrier under the respective pH conditions thus examined, thereby controlling conductivity.

For example, elution conditions under which only affinity of neuraminidase for the carrier is reduced can be selected by gradually increasing the salt concentration by adding each 10 mmol/L of sodium chloride to an elution buffer under acidic condition (e.g., pH 6.0) where both neuraminidase and Antithrombin are adsorbed onto the carrier.

The procedures as described above are performed so as to determine optimum combinations of pH and salt concentration or conductivity where neuraminidase does not affect Antithrombin quality and the conditions for removing neuraminidase by intermediate washing.

Examples of the buffer used in this process may include phosphate, citrate, acetate, succinate, maleate, borate, Tris (base), HEPES, MES, PIPES, MOPS, TES, Tricine or the like.

The concentration thereof is preferably 0.001 mol/L to 0.5 mol/L, and more preferably 0.01 to 0.2 mol/L. Further, the salt may be used in a combination of 0.001 mol/L to 4 mol/L of other salt such as sodium chloride, potassium chloride, calcium chloride, sodium citrate, sodium sulfate, ammonium sulfate or the like. Further, the wash buffer generally has different ingredients and conditions from those of the buffer used for adsorbing the objective protein onto the carrier in the first process described above.

Further, the buffer used for chromatography or for washing may be a "buffer containing amino acids". The buffer containing amino acids may include a buffer containing sugars, enzyme inhibitors or the like in addition to amino acids.

Examples of the amino acids, sugars, or enzyme inhibitors may include amino acids such as glycine, alanine, arginine, serine, threonine, glutamic acid, aspartic acid, histidine or the like and derivatives thereof, and glucose, sucrose, lactose or sialic acid and derivatives thereof.

Specific examples thereof may include 20 mmol/L sodium phosphate (pH 6.0) containing 300 mmol/L glycine, 20 mmol/L sodium phosphate (pH 6.0) containing 100 mmol/L sodium chloride, 20 mmol/L sodium phosphate (pH 7.0) or the like. The purified protein with the desired quality can be obtained by using these buffers, and these buffers can be applied to a variety of chromatographies, in addition to the mixed mode chromatography.

The objective protein adsorbed onto the mixed mode carrier is eluted by increasing the salt concentration or conductivity of the buffer, or by varying pH of the buffer. During this procedure, the objective protein and impurities are separated.

In the present invention, the "buffer weakening affinity of impurities for the mixed mode carrier" may be exemplified by a buffer generating a difference in affinity for the carrier between the impurities and the objective protein. Specific example thereof may include a buffer having a proper pH and salt concentration (or conductivity). pH of the buffer is preferably pH 4 to 9, and more preferably pH 5 to 8.

Conductivity of the buffer is preferably 0.01 to 300 mS/cm, and more preferably 0.1 to 250 mS/cm. A proper pH at which a difference in affinity occurs can be selected from combinations of ion exchange group and hydrophobic interaction group in the mixed mode carrier by those skilled in the art, it can be also determined with reference to isoelectric points of the objective protein and impurities.

For example, in Example 1 described below, pH at which neuraminidase and Antithrombin are eluted separately is determined by gradually increasing pH from pH 6.0, at which both Antithrombin and neuraminidase are adsorb onto the mixed mode carrier, to basic side.

Subsequently, the salt concentration of the buffer for elution, at which neuraminidase and Antithrombin are eluted separately, is determined, for example, by gradually increasing 10 mmol/L of the salt concentration under the respective pH conditions.

Further, the most preferable conditions for the separation of neuraminidase and Antithrombin are selected from the combinations of pH and salt concentration thus examined.

The elution method may be any one of an elution method of applying a buffer having a particular salt concentration or pH at which affinity of the objective protein and the mixed mode carrier is reduced (one-step elution), an elution method of stepwisely varying the salt concentration or pH (stepwise method), and an elution method of continuously varying the salt concentration or pH (gradient method).

Examples of the buffer for elution may include phosphate, citrate, acetate, succinate, maleate, borate, Tris (base), HEPES, MES, PIPES, MOPS, TES, Tricine or the like.

The concentration thereof is preferably 0.001 mol/L to 0.5 mol/L, and more preferably 0.01 to 0.2 mol/L. Further, the salt may be used in a combination of 0.001 mol/L to 4 mol/L of other salt such as sodium chloride, potassium chloride, calcium chloride, sodium citrate, sodium sulfate, ammonium sulfate or the like.

Further, the buffer may include amino acids, sugars, enzyme inhibitors or the like. Examples thereof may include amino acids such as glycine, alanine, arginine, serine, threonine, glutamic acid, aspartic acid, histidine or the like and derivatives thereof, glucose, sucrose, lactose, sialic acid or the like.

Specific examples thereof may include 5 to 500 mmol/L sodium phosphate buffer (pH 4 to 8) containing 0 to 1 mol/L sodium chloride, 5 to 500 mmol/L sodium citrate (pH 4 to 7) containing 0 to 1 mol/L sodium chloride, or the like.

In the first step of the second process, the objective protein and impurities are separated by selecting any one of the processes for washing and eluting the objective protein adsorbed onto the carrier or by combinations of both processes.

In the present invention, an inhibitor for inhibiting neuraminidase activity can be used. Examples of the inhibitor may include sialic acid, amino acids, divalent metal ions, or the like. Examples of the amino acids may include amino acids such as glycine, alanine, arginine, serine, threonine, glutamic acid, aspartic acid, histidine or the like and derivatives thereof.

These amino acids are used in the chromatographic process, intermediates during the purification process, or a pool liquid. The concentration thereof is preferably 0.001 mol/L to 4 mol/L, and more preferably 0.1 mol/L to 1 mol/L.

The amino acids are added to the equilibration buffer, the wash buffer, or/and the protein composition as a starting material at these concentrations, thereby inhibiting elimination of sialic acid from the objective protein. Meanwhile, inhibition of neuraminidase by addition of amino acids is not limited to the purification process using the mixed mode carrier of the present invention, and can be applied to any production process.

The second step of the second process of the present invention, "process of recovering a particular range of fractions of the eluate", is performed to reduce impurities to the desired level by recovering the particular range of fractions after elution of the objective protein from the mixed mode carrier.

In order to determine the fraction range, one or more fractions containing the objective protein with the desired quality may be selected by preparing two or more fractions of the eluate in advance, and measuring the contents of the objective protein and impurities in the respective fraction. Through this procedure, the fraction range with the desired quality can be specified, excluding the fraction containing a large amount of impurities.

In the end of the chromatography of the first process, preferably 50% or more, more preferably 70% or more, and much more preferably 80% or more of the objective protein is recovered from the protein composition, and impurities related to the quality of the protein itself are removed to obtain a protein solution with stable quality by using the technology of the present invention.

The purified protein with the "desired quality" can be obtained by using the technology of the present invention. For example, the "desired quality" means that the number of bound sialic acids per the objective protein is preferably 70% or more, and more preferably 80% or more of the maximum number to be added.

For example, the "desired quality" also means that the content of the aggregate or cleaved form is reduced to preferably 10% or less, more preferably 5% or less, and much more preferably 1% or less.

Specifically, the purified protein with the desired quality may include Antithrombin α form having 6 mol/mol or more of the number of bound sialic acids per 1 molecule, Antithrombin β form having 4 mol/mol or more of the number of bound sialic acids per 1 molecule, a mixture of the Antithrombin α and β forms, Erythropoietin having 8 mol/mol or more of the number of bound sialic acids per 1 molecule, Protein S having 5 mol/mol or more of the number of bound sialic acids per 1 molecule, Antithrombin having the aggregate content of 1% or less, Erythropoietin having the aggregate content of 1% or less, Protein S having the aggregate content of 10% or less, Protein S having the content of cleaved form of 10% or less, or the like.

The present invention relates to a method for purifying a protein, including a first chromatographic process including the following processes of (a) to (c):

(a) a process of contacting a protein composition with an anion exchange carrier;

(b) a process of washing and/or eluting the anion exchange carrier using a buffer weakening affinity of impurities for the anion exchange carrier so as to remove impurities; and (c) a process of washing and/or eluting the anion exchange carrier using a buffer containing amino acids so as to remove impurities.

To the processes of (a) to (c), (d), a process of obtaining only a fraction of the purified protein with the desired quality, may be added.

Further, the present invention relates to a purification method for obtaining the purified protein with the desired quality by proper combinations of contacting the protein composition such as culture supernatant or the like with the anion exchange carrier, rapidly separating or reducing components producing objective protein-derived impurities or the objective protein-derived impurities themselves from the protein composition, using a buffer containing amino acids, and selecting an elution fraction.

In the present invention, when the anion exchange carrier is used, a distinctive procedure for purifying the objective protein from the protein composition may be performed, for example, in this order: (1) a process of contacting the protein composition with the anion exchange carrier so as to adsorb the objective protein thereto, and (2) a process of controlling quality of the objective protein. The process of (2) is further divided into (2-1) a process of separating impurities so as to elute the objective protein and (2-2) a process of recovering a particular range of fractions of the eluate.

In the present invention, the anion exchange carrier used in the first chromatography process may be a carrier or membrane prepared by directly or indirectly immobilizing anion exchange groups onto a solid-phase matrix. The anion exchange group, the solid-phase matrix, and immobilization of the anion exchange groups onto the solid-phase matrix are the same as described above.

Specific examples thereof may include Q Sepharose XL, Q Sepharose FF, DEAE Sepharose FF, ANX Sepharose FF, Capto Q, Capto DEAE, Capto Q ImpRes (all manufactured by GE Healthcare), TOYOPEARL GigaCap Q-650, TOYOPEARL SuperQ-650 (all manufactured by TOSOH Corporation), Fractogel DEAE, Fractogel TMAE, Fractogel TMAE Hicap, Eshmuno Q (all manufactured by Merck), Cellufine MAX-Q (manufactured by INC) or the like, but are not limited thereto.

The first process of the present invention, "process of contacting the protein composition with the anion exchange carrier to adsorb the objective protein thereto" is performed in a capture mode (adsorption mode). The above described protein composition is applied to a column packed with the anion exchange carrier so as to adsorb the objective protein onto the carrier.

The condition for adsorbing the protein onto the anion exchange carrier may be preferably pH 4 to 9, and more preferably pH 5 to 8. The adsorption amount of the protein per 1 mL of the carrier is preferably 1 to 100 mg, and more preferably 5 mg or more.

Conductivity is preferably 0.01 mS/cm to 50 mS/cm, and more preferably 0.1 to 30 mS/cm. The amount of the anion exchange carrier is determined such that preferably 50% or more, more preferably 70% or more, and much more preferably 80% or more of the objective protein included in the protein composition are adsorbed, and the protein is recovered in the process yield of preferably 50% or more, more preferably 70% or more, and much more preferably 80% or more.

In the first step of the second process of the present invention, "process of separating impurities and eluting the objective protein", impurities are removed or separated to a desired level until the objective protein is eluted from the anion exchange carrier.

The first impurities to be removed or separated may include components generating the objective protein-derived impurities, that is, components changing the properties of the objective protein, as described above. The second impurities to be removed or separated are mainly those derived from the objective protein, which are generated by the above described first impurities.

This process may be performed by the following procedures. The objective protein is adsorbed onto the anion exchange carrier, and then washed with a buffer to wash and remove the impurities. The buffer conditions for washing impurities are selected from the conditions under which impurities are not adsorbed while the objective protein are adsorbed, or affinity between the impurities and the carrier is reduced, by varying pH, conductivity, ingredients of the buffer, salt concentration, additive or the like.

In the selection of the conditions, differences in physicochemical properties between impurities and the objective protein, for example, differences in isoelectric point, charge, hydrophobicity, molecular size, conformation or the like may be employed. These differences may occur by elimination of sialic acid from the objective protein, changes in charge, oxidation, changes in hydrophobicity or molecular size by aggregation or cleavage, denaturation depending on solution conditions, or the like.

Specific conditions of the buffer used for washing selected from the conditions under which changes in affinity of impurities and the objective protein for the anion exchange carrier are generated, preferably pH 4 to 9, and more preferably pH 5 to 8.

Conductivity is preferably 0.01 to 300 mS/cm, and more preferably 0.1 to 250 mS/cm. A proper pH at which a difference in affinity occurs can be selected from anion exchange groups in the anion exchange carrier by those skilled in the art, but it can be also determined with reference to isoelectric points of the objective protein and impurities as described above.

Examples of the buffer used in this process may include phosphate, citrate, acetate, succinate, maleate, borate, Tris (base), HEPES, MES, PIPES, MOPS, TES, Tricine or the like.

The concentration thereof is preferably 0.001 mol/L to 0.5 mol/L, and more preferably 0.01 to 0.1 mol/L. Further, the above mentioned salt may be used in a combination of 0.001 mol/L to 4 mol/L of other salt such as sodium chloride, potassium chloride, calcium chloride, sodium citrate, sodium sulfate, ammonium sulfate or the like. Further, the wash buffer generally has different ingredients and conditions from those of the buffer used for adsorbing the objective protein onto the carrier in the first process described above.

Further, the buffer used for chromatography or for washing may be a "buffer containing amino acids". The buffer containing amino acids may include a buffer containing sugars, enzyme inhibitors or the like in addition to amino acids.

Examples of the amino acids may include amino acids such as glycine, alanine, arginine, serine, threonine, glutamic acid, aspartic acid, histidine or the like and derivatives thereof, and examples of the sugars may include glucose, sucrose, lactose or sialic acid and derivatives thereof as described above. These buffers can be used to obtain the purified protein with the desired quality, and applied to a variety of chromatographies.

The objective protein adsorbed onto the anion exchange carrier is eluted by increasing the salt concentration or conductivity of the buffer, or by varying pH of the buffer. During this procedure, the objective protein and impurities are separated.

In the present invention, the "buffer weakening affinity of impurities for the anion exchange carrier" may be exemplified by a buffer generating a difference in affinity for the carrier between the impurities and the objective protein. Specific example thereof may include a buffer having a proper pH and salt concentration (or conductivity).

pH of the corresponding buffer is preferably pH 4 to 9, and more preferably pH 5 to 8. Conductivity of the buffer is preferably 0.01 to 300 mS/cm, and more preferably 0.1 to 250 mS/cm.

A proper pH at which a difference in affinity occurs can be selected from anion exchange groups in the anion exchange carrier by those skilled in the art, but it can be also determined with reference to isoelectric points of the objective protein and impurities as described above.

The elution method may be any one of an elution method of applying a buffer having a particular salt concentration or pH at which affinity of the objective protein and the anion exchange carrier is reduced (one-step elution), an elution method of stepwise varying the salt concentration or pH (stepwise method), and an elution method of continuously varying the salt concentration or pH (gradient method).

Examples of the buffer for elution may include phosphate, citrate, acetate, succinate, maleate, borate, Iris (base), HEPES, MES, PIPES, MOPS, TES, Tricine or the like.

The concentration thereof is preferably 0.001 mol/L to 0.5 mol/L, and more preferably 0.01 to 0.1 mol/L. Further, the above mentioned salt may be used in a combination of 0.001 mol/L to 4 mol/L of other salt such as sodium chloride, potassium chloride, calcium chloride, sodium citrate, sodium sulfate, ammonium sulfate or the like.

Further, the buffer may include amino acids, sugars, enzyme inhibitors or the like. Examples thereof may include amino acids such as glycine, alanine, arginine, serine, threonine, glutamic acid, aspartic acid, histidine or the like and derivatives thereof, and glucose, sucrose, lactose, sialic acid or the like.

Specific examples thereof may include 5 to 500 mmol/L sodium phosphate buffer (pH 4 to 8) containing 0 to 1 moUL sodium chloride, 5 to 500 mmol/L sodium citrate (pH 4 to 7) containing 0 to 1 mol/L sodium chloride, or the like.

In the first step of the second process, the objective protein and impurities are separated by selecting any one of the processes for washing and eluting the objective protein adsorbed onto the carrier or by combinations of both processes.

In the present invention, an inhibitor for inhibiting neuraminidase activity can be used. Examples of the inhibitor may include sialic acid, amino acids, divalent metal ions, and the like. Examples of the amino acids may include amino acids such as glycine, alanine, arginine, serine, threonine, glutamic acid, aspartic acid, histidine or the like and derivatives thereof.

These amino acids are used in the chromatographic process, intermediates during the purification process or a pool liquid. The concentration thereof is preferably 0.001 mol/L to 4 mol/L, and more preferably 0.1 mol/L to 1 mol/L.

The amino acids are added to the equilibration buffer, the wash buffer, or/and the protein composition as a starting material at these concentrations, thereby inhibiting elimination of sialic acid from the objective protein. Meanwhile, inhibition of neuraminidase by addition of amino acids is not limited to the purification process using the anion exchange carrier of the present invention, and can be applied to any production process.

The second step of the second process of the present invention, "process of recovering a particular range of fractions of the eluate", is performed to reduce impurities to the desired level by recovering the particular range of fractions after elution of the objective protein from the anion exchange carrier.

In order to determine the fraction range, one or more fractions containing the objective protein with the desired quality may be selected by preparing two or more fractions of the eluate in advance, and measuring the contents of the objective protein and impurities in the respective fraction. Through this procedure, the fraction range with the desired quality can be specified, excluding the fraction containing a large amount of impurities.

In the end of the chromatography of the first process, preferably 50% or more, more preferably 70% or more, and much more preferably 80% or more of the objective protein is recovered from the protein composition, and impurities related to the quality of the protein itself are removed to obtain a protein solution with stable quality by using the technology of the present invention. The purified protein with the "desired quality" can be obtained by using the technology of the present invention, as described above.

In the present invention, the protein composition is purified using the mixed mode carrier or anion exchange carrier in the first chromatographic process, and subsequently purified by combinations of the conventional purification methods, thereby providing a protein composition with a high purity for pharmaceutical use.

Examples of the conventional purification methods may include combinations of one or more chromatographies using any one carrier or membrane selected from mixed mode carriers, anion exchange carriers, cation exchange carriers, hydrophobic interaction carriers, size exclusion carriers, gel filtration carriers, reversed-phase carriers, hydroxyapatite carriers, fluorapatite carriers, sulfated cellulose carriers, sulfated agarose carriers and the like, or membranes. Further, unit manipulations such as buffer exchange, concentration, dilution, filtration, virus inactivation, virus removal or the like may be properly applied.

Examples of the mixed mode carrier may include the above described mixed mode carriers. Specific examples thereof may include Capto adhere, Capto MMC (all manufactured by GE Healthcare), HEA HyperCel, PPA HyperCel, MEP HyperCel (all manufactured by Pall Corp.), TOYOPEARL MX-Trp-650M (manufactured by TOSOH Corporation) or the like, but are not limited thereto.

Examples of the anion exchange carrier may include a carrier or membrane prepared by directly or indirectly immobilizing anion exchange groups onto a solid-phase matrix. The anion exchange group, the solid-phase matrix, and immobilization of the anion exchange groups onto the solid-phase matrix are the same as described above.

Specific examples thereof may include Q Sepharose XL, Q Sepharose FF, DEAE Sepharose FF, ANX Sepharose FF, Capto Q, Capto DEAE, Capto Q ImpRes (all manufactured by GE Healthcare), TOYOPEARL GigaCap Q-650, TOYOPEARL SuperQ-650 (all manufactured by TOSOH Corporation), Fractogel DEAE, Fractogel TMAE, Fractogel TMAE Hicap, Eshmuno Q (all manufactured by Merck), Cellufine MAX-Q (manufactured by JNC) Mustang Q (manufactured by Pall), Sartobind Q, Sartobind STIC (all manufactured by Sartorius) or the like, but are not limited thereto.

Examples of the cation exchange carrier may include a carrier or membrane prepared by directly or indirectly immobilizing cation exchange groups onto a solid-phase matrix. The cation exchange group, the solid-phase matrix, and immobilization of the cation exchange groups onto the solid-phase matrix are the same as described above.

Specific examples thereof may include SP Sepharose FF, CM Sepharose FF, SP Sepharose XL, Capto S (all manufactured by GE Healthcare), Poros 50 HS, Poros 50 XS (all manufactured by Applied Biosystems), Eshmuno S, Fractogel COO—, Fractogel SO3-, Fractogel SE Hicap (all manufactured by Merck), TOYOPEARL GigaCap S-650, TOYOPEARL GigaCap CM-650 (al manufactured by TOSOH Corporation), Cellufine MAX-S (manufactured by JNC), Mustang S (manufactured by Pall), Sartobind S (manufactured by Sartorius) or the like, but are not limited thereto.

Examples of the hydrophobic interaction carrier may include a carrier prepared by directly or indirectly immobilizing hydrophobic interaction groups onto a solid-phase matrix. The hydrophobic interaction group, the solid-phase matrix, and immobilization of the hydrophobic interaction groups onto the solid-phase matrix are the same as described above.

Specific examples thereof may include Phenyl Sepharose, Butyl Sepharose, Octyl Sepharose (all manufactured by GE Healthcare), TOYOPEARL SUPER BUTYL-550C, TOYOPEARL BUTYL-650C, TOYOPEARL BUTYL-600M, TOYOPEARL PHENYL-650, TOYOPEARL PPG-600M, TOYOPEARL Ether-650M, TOYOPEARL Hexyl-650C, TSKgel Phenyl-5PW (all manufactured by TOSOH Corporation), Macroprep HIC carrier series (manufactured by Bio-Rad), Cellufine Phenyl, Cellufine Butyl (all manufactured by JNC), Butylated Chitopearl, Phenylated Chitopearl (all manufactured by HUJIBO Holdings, inc.) or the like, but are not limited thereto.

Examples of the carrier for reversed-phase chromatography may include a carrier prepared by directly or indirectly immobilizing hydrocarbon groups onto a solid-phase matrix. Examples of the hydrocarbon groups may include trimethyl groups, butyl groups, phenyl groups, octyl groups or octadecyl groups, and end-modified functional groups thereof.

The solid-phase matrix and immobilization of the hydrophobic interaction groups onto the solid-phase matrix are the same as described above. Specific examples thereof may include RESOURCE RPC series, SOURCE RPC series (all manufactured by GE Healthcare) or the like, but are not limited thereto.

Examples of the size exclusion carrier or gel filtration carrier may include carriers that are composed of polymers consisting of dextran, allyl dextran, N,N'-methylenebisacrylamide, cellulose, agarose, styrene, divinylbenzene, polyvinyl alcohol, silica, chitosan or the like.

Specific examples thereof may include Sephacryl S series, Sepharose series, Sephadex series, Superdex series, Sephacryl series (all manufactured by GE Healthcare), TOYOPEARL HW series, TSKgel PW series (all manufactured by TOSOH Corporation), Bio gel Agarose, Bio gel P Polyacrylamide (all manufactured by Bio-Rad), Cellufine GH, Cellufine GCL (all manufactured by JNC), Trisacryl GF05, Trisacryl GF2000, Ultrogel AcA (all manufactured by Pall Corp.), Fractogel BioSEC (manufactured by Merck) or the like, but are not limited thereto.

Examples of the hydroxyapatite carrier may include CHT Ceramic Hydroxyapatite Type I or Type II (all manufactured by Bio-Rad), but are not limited thereto. Further, examples of the fluoroapatite carrier may include CFT Ceramic Fluoroapatite (manufactured by Bio-Rad) or the like, but are not limited thereto.

Examples of the sulfated cellulose carriers or the agarose sulfate carriers may include Cellufine Sulfate, Cellufine Sulfate m, Cellufine Sulfate c, Sulfated Cellulofine m, Sulfated Cellulofine c, Sulfated Cellufine m, Sulfated Cellufine c (all manufactured by JNC), Capto DeVirS (manufactured by GE Healthcare) or the like, but are not limited thereto.

In the conventional purification methods, the chromatography using the carrier or membrane may be performed in a capture mode (adsorption mode) or flow-through mode (non-adsorption mode), depending on the purpose. The buffer used in chromatography or washing is selected by varying pH, conductivity, ingredients of the buffer, salt concentration, additive or the like, so as to be preferable condition.

In the selection of the conditions, differences in physicochemical properties between impurities and the objective protein, for example, differences in isoelectric point, charge, hydrophobicity, molecular size or conformation or the like may be employed. The elution method of capture mode may be any one of an elution method of applying a buffer having a particular salt concentration or pH at which affinity of the objective protein and the carrier is reduced (one-step elution), an elution method of stepwisely varying the salt concentration or pH (stepwise method), and an elution method of continuously varying the salt concentration or pH (gradient method).

The objective protein with the quality demanded as pharmaceuticals can be obtained by combinations of the above mentioned processes.

For example, Antithrombin, Erythropoietin, Protein S, or derivative thereof that maintains the binding ratio of the sialic acid of 70% or more, and preferably 80% or more can be obtained with a sufficient purity for pharmaceutical use. Further, Antithrombin, Erythropoietin, Protein S, or derivative thereof that has the reduced content of aggregate or cleaved form of 10% or less, preferably 5% or less, and more preferably 1% or less can be obtained.

In the present invention, the number of bound sialic acids is the average number of sialic acids molecule (mol/mol) binding to 1 molecule of the protein. Specifically, it can be measured by, for example, a fluorescent HPLC [Anal. Biochem., 164, 138 (1987)], a resorcinol method, or the like. The number of bound sialic acids can be also measured by, for example, isoelectric focusing electrophoresis, capillary isoelectric focusing electrophoresis, or the like.

The binding ratio of sialic acid represents a ratio of the measured number of bound sialic acids to the theoretical maximum number of bound sialic acids (the maximum number to be added) in the protein. The theoretical maximum number of bound sialic acids is, for example, 8 mol/mol for Antithrombin α form, 6 mol/mol for Antithrombin β form, 14 mol/mol for Erythropoietin, and 6 mol/mol for Protein S.

In the present invention, the content of the aggregate and cleaved form in Antithrombin, Erythropoietin, Protein S, or derivatives thereof may be also measured by a gel filtration HPLC method, polyacrylamide gel electrophoresis, light scattering, an ultracentrifugal method, or the like.

With respect to the use of the present invention, the protein purification can be used as a main ingredient in pharmaceuticals, diagnostic agents, foods, chemical industry products, or the like.

The present invention relates to a composition including the protein that is purified by the above described protein purification method.

In the present invention, examples of the composition including the purified protein may include drug formulations.

It is possible to administer the drug formulations of the present invention including the purified protein alone as a prophylactic or therapeutic agent. However, the drug formulation is preferably provided as a formulation that is prepared by mixing with one or more typical pharmaceutically acceptable additives or the like by any method well known in the technical field of pharmaceutics.

Examples of the formulations may include spray, capsule, tablet, granule, syrup, emulsion, suppository, injectable formulation, ointment, tape or the like.

Formulations suitable for oral administration may include emulsion, syrup, capsule, tablet, powder, granule or the like.

The liquid formulations such as emulsion and syrup can be prepared by using water, a saccharide such as sucrose, sorbitol and fructose, glycol such as polyethylene glycol and propylene glycol, oil such as sesame oil, olive oil and soybean oil, an antiseptic such as p-hydroxybenzoate esters, or a flavor such as strawberry flavor and peppermint.

The capsule, tablet, powder or granules can be produced by using an excipient such as lactose, glucose, sucrose and mannitol, a disintegrator such as starch and sodium alginate, a lubricant such as magnesium stearate and talc, a binder such as polyvinyl alcohol, hydroxypropyl cellulose and gelatin, a surfactant such as a fatty acid ester, a placticizer such as glycerin, or the like.

Formulations suitable for parenteral administration may be exemplified by injectable formulations, suppository, spray and the like.

Injectable formulations are prepared by using an additive composed of a salt solution or a glucose solution, or a mixture thereof. Alternatively, the purified protein is freeze-dried according to the typical method, and sodium chloride is added thereto, thereby preparing a powder injectable formulation.

Suppositories are prepared by using additives such as cacao butter, hydrogenated fat, carboxylic acids or the like.

Further, spray formulations are prepared by using the purified protein itself, or by using a carrier that disperses the purified protein as microparticles for easy absorption without irritating oral cavity and the oropharyngeal mucous membrane of a recipient.

Specific examples of the additive may include lactose, glycerin or the like. Formulations such as aerosol or dry powder are possible depending on the properties of the purified protein and the carrier to be used. The ingredients exemplified as the additive for oral formulations may be also added to the parenteral formulations.

The present invention relates to a method for purifying Antithrombin with the desired quality by proper combinations of directly contacting an Antithrombin composition such as culture supernatant or the like with the mixed mode carrier or anion exchange carrier, rapidly separating or reducing components producing impurities from the Antithrombin composition or impurities themselves, using a buffer containing amino acids, and selecting an elution fraction.

The Antithrombin composition such as culture supernatant or the like may be obtained by, for example, the method described in WO 2008/120801.

The carrier used in the mixed mode carrier or anion exchange carrier in the first chromatographic process, and the purification method of the first chromatographic process are the same as described above.

The Antithrombin composition is purified using the mixed mode carrier or anion exchange carrier in the first chromatographic process, and subsequently purified by combinations of the conventional purification methods, thereby providing Antithrombin with a high purity for pharmaceutical use.

The conventional purification method may be preferably a purification method including at least one of anion exchange carrier, anion exchange membrane, sulfated cellulose carrier, sulfated agarose carrier, or hydrophobic interaction carrier, as described above.

Example thereof may include a purification method for obtaining purified Antithrombin using the anion exchange carrier or anion exchange membrane in the second chromatographic process, the sulfated cellulose carrier or sulfated agarose carrier in the third chromatographic process, and the hydrophobic interaction carrier in the fourth chromatographic process.

The number of bound sialic acids of the purified Antithrombin thus obtained by the above purification method is 70% or more of the maximum number to be added.

The present invention relates to a method for purifying Protein S with the desired quality by proper combinations of directly contacting a Protein S composition such as culture supernatant or the like with the mixed mode carrier, rapidly separating or reducing components producing impurities from the Protein S composition or impurities themselves, using a buffer containing amino acids, and selecting an elution fraction.

The Protein S composition such as culture supernatant or the like may be obtained by, for example, the method described in WO 2010/018847.

The carrier used in the mixed mode carrier in the first chromatographic process, and the purification method of the first chromatographic process are the same as described above.

The Protein S composition is purified using the mixed mode carrier in the first chromatographic process, and subsequently purified by combinations of the conventional purification methods, thereby providing Protein S with a high purity for pharmaceutical use. The conventional purification method may be preferably a purification method using at least one of anion exchange carrier, anion exchange membrane, or a hydroxyapatite carrier, as described above.

Example thereof may include a purification method for obtaining purified Protein S including the anion exchange carrier in the second chromatographic process, and the hydroxyapatite carrier in the third chromatographic process.

EXAMPLES

Hereinafter, the present invention will be described in more detail with reference to Examples. However, the present invention is not limited to these Examples.

Example 1

Example of a Method for Removing Sialidase from an Antithrombin Culture Supernatant Using a Mixed Mode Carrier to Recover an Object A CHO cell culture supernatant containing about 380 mg of Antithrombin was directly passed through a mixed mode column (manufactured by GE Healthcare, Capto adhere, column volume: 38 mL) equilibrated with buffer AA (100 mmol/L sodium chloride, 20 mmol/L sodium phosphate buffer, pH 6.0) to adsorb Antithrombin thereto.

The column was washed with 195 mL of buffer AA (100 mmol/L sodium chloride, 20 mmol/L sodium phosphate buffer, pH 6.0), and then 152 mL of buffer AB (350 mmol/L sodium chloride, 20 mmol/L sodium phosphate buffer, pH 7.0) was applied to elute Antithrombin.

The Antithrombin concentration and the neuraminidase activity in the washing fraction before elution and in a particular range of eluate were measured by reversed-phase HPLC method [J. Chromatography B, 662, 209 (1994)] and enzyme assay [Glycobiology, 3, 455 (1993)], respectively. The results are shown in Table 1.

TABLE 1

Separation of Antithrombin and neuraminidase by mixed mode chromatography of Example 1

| | Antithrombin concentration (g/L) | Neuraminidase activity (U/L) |
|---|---|---|
| Washing fraction before elution | Not detected | 28.4 |
| Eluate | 2.80 | Not detected |

As shown in Table 1, the recovery of Antithrombin in the predetermined eluate was as good as 84%. Neuraminidase was eluted in the washing fraction before elution and Antithrombin was eluted in eluate.

Under the conditions of Comparative Example 1, the neuraminidase activity was also detected in the Antithrombin eluate. However, it was found that the condition of the buffer used for washing before elution was controlled at pH weakening the affinity of neuraminidase for the mixed mode carrier, thereby directly separating Antithrombin and neuraminidase from the culture supernatant by the mixed mode chromatography in a very effective manner.

That is, the culture supernatant was directly passed through the mixed mode carrier, Antithrombin was adsorbed onto the carrier, neuraminidase was removed by washing, Antithrombin was eluted, and the range of eluate was determined by HPLC, thereby obtaining a composition from which neuraminidase as a factor affecting Antithrombin quality (number of bound sialic acids) was effectively removed.

Example 2

Example of Controlling the Number of Bound Sialic Acids of Antithrombin Using the Mixed Mode Carrier (Example of a Method for More Increasing the Number of Bound Sialic Acids Using a Glycine Buffer)

A CHO cell culture supernatant containing about 380 mg of Antithrombin was directly passed through a mixed mode column (manufactured by GE Healthcare, Capto adhere, column volume: 38 mL) equilibrated with buffer AC (300 mmol/L glycine, 100 mmol/L sodium chloride, 20 mmol/L sodium phosphate buffer, pH 6.0) to adsorb Antithrombin thereto.

The column was washed with 195 mL of buffer AC containing glycine (300 mmol/L glycine, 100 mmol/L sodium chloride, 20 mmol/L sodium phosphate buffer, pH 6.0), and then 152 mL of buffer AB (350 mmol/L sodium chloride, 20 mmol/L sodium phosphate buffer, pH 7.0) was applied to elute Antithrombin. The number of bound sialic acids of Antithrombin recovered in the particular range of fractions after elution was measured in the same manner as in Example 1.

As a result, when purification was performed under the conditions of Example 2 (buffer AC used for equilibration and washing before elution), the number of bound sialic acids was increased to 1.3-fold, compared to the purification conditions of Example 1 (buffer AA used for equilibration and washing before elution). It can be seen that quality (number of bound sialic acids) of Antithrombin eluted can be more improved by addition of glycine to the buffer used for washing before elution.

Example 3

Example of Controlling the Number of Bound Sialic Acids of Antithrombin Using the Mixed Mode Carrier (Example Showing that the Glycine Buffer can be Replaced by Other Amino Acid Buffer in Example 2)

Arginine hydrochloride or glycine of a final concentration of 0 to 500 mmol/L was added to the aqueous solution containing Antithrombin obtained in the elution process of Comparative Example 1. The neuraminidase activity in each solution was measured in the same manner as in Example 1. The results are shown in FIG. 1.

As shown in FIG. 1, when the neuraminidase activity at the loading amount of amino acid of 0 mmol/L was regarded as 1.0, the relative activity was about 0.2 by addition of 100 mmol/L of arginine hydrochloride or glycine. Further, the relative activity was 0 (below the detection limit) by addition of 200 mmol/L or more of arginine, or 300 mmol/L or more of glycine.

These results indicate that purification as in Example 2 can be performed by replacement of glycine with other amino acid such as arginine or the like.

Example 4

Example of Purification of Antithrombin α Form by Combinations of the Mixed Mode Carrier and Other Chromatographies A CHO cell culture supernatant containing about 1.43 g of Antithrombin was purified in the same manner as in Example 2 (except that buffer AD (450 mmol/L sodium chloride, 20 mmol/L sodium phosphate buffer, pH 6.0) was used instead of buffer AC), and the particular range thereof was recovered, thereby obtaining 236 mL of the recovered liquid. The recovery of Antithrombin in this process was as good as 80%.

The aqueous solution containing Antithrombin recovered in the above mentioned process was mixed with Triton X-100 and tributyl phosphate at their concentrations of 1% and 0.3%, respectively, followed by gently stirring. This solution was diluted several-fold with purified water, and then it was passed through the column (manufactured by Merck Millipore, Eshmuno Q, column volume: 19.6 mL) equilibrated with buffer AE (20 mmol/L sodium phosphate buffer, pH 7.0) to adsorb Antithrombin thereto.

The column was washed using 3 column volumes of buffer AE (20 mmol/L sodium phosphate buffer, pH 7.0), and then 4 column volumes of buffer AB (350 mmol/L sodium chloride, 20 mmol/L sodium phosphate buffer, pH 7.0) was applied to elute Antithrombin.

Sodium phosphate buffer or purified water was added to the aqueous solution containing Antithrombin recovered in the above mentioned process, and pH and conductivity were adjusted to 6.0 and 25.2 mS/cm, respectively. This solution was passed through the column (manufactured by JNC, Cellufine Sulfate, column volume: 23.7 mL) equilibrated with buffer AF (170 mmol/L sodium chloride, 20 mmol/L sodium phosphate buffer, pH 6.0) to recover and neutralize a solution that was passed through the column.

Several-fold dilution of the aqueous solution containing Antithrombin thus recovered in the above mentioned process was carried out using buffer AG (1.5 mol/L sodium citrate, 20 mmol/L sodium phosphate buffer, pH 7.0). This solution was passed through the column (manufactured by GE Healthcare, Phenyl Sepharose 6 Fast Flow, column volume: 4.9 mL) equilibrated with buffer AH (1 mol/L sodium citrate, 20 mmol/L sodium phosphate buffer, pH 8.0) to adsorb Antithrombin thereto.

The column was washed with 2 column volumes of buffer AH (1 mol/L sodium citrate, 20 mmol/L sodium phosphate buffer, pH 8.0), and then Antithrombin was eluted with a linear gradient of sodium citrate.

The aqueous solution containing Antithrombin thus recovered in the above mentioned process was concentrated using an ultrafiltration membrane (manufactured by Merck Millipore, a molecular weight cut off: 10 kilodaltons) to a proper concentration, and then the buffer was exchanged with buffer AI (20 g/L glycine, 12 g/L sodium citrate buffer, pH 7.5). The number of bound sialic acids of this solution was measured in the same manner as in Example 1.

As a result, the number of bound sialic acids was calculated as 6.7 mol/mol (binding ratio: 84%), indicating that Antithrombin α form having the number of bound sialic acids of 6 or more (binding ratio: 75% or more) can be purified by a combination of the multi-mode carrier and different chromatography process.

Example 5

Comparison of Mixed Mode Carrier and Anion Exchange Carrier in the Direct Recovery of Antithrombin from the Culture Supernatant Each 1 mL of Capto adhere manufactured by GE Healthcare, Q Sepharose Fast Flow manufactured by GE Healthcare, Eshmuno Q manufactured by Merck Millipore, and Toyopearl Q-600C AR manufactured by TOSOH Corporation were aliquoted in tubes, and equilibrated with buffer AE (20 mmol/L sodium phosphate buffer, pH 7.0) and used as 50% slurries (total 2 mL).

The CHO cell culture supernatant (11 mL) containing Antithrombin was directly added to the slurries, and stirred at room temperature overnight. After completion of stirring, the Antithrombin concentration in the supernatant was measured in the same manner as in Example 1. The adsorption amount of Antithrombin (g) per unit volume of carrier (1 L) was calculated from the reduced amount of Antithrombin in the culture supernatant by the following Equation. The results are shown in FIG. 2.

(Adsorption amount of Antithrombin (g) per unit volume of carrier (1 L))=[(Antithrombin amount in culture supernatant)−(Antithrombin amount in carrier-treated supernatant)]/(carrier volume)

Figure 2:
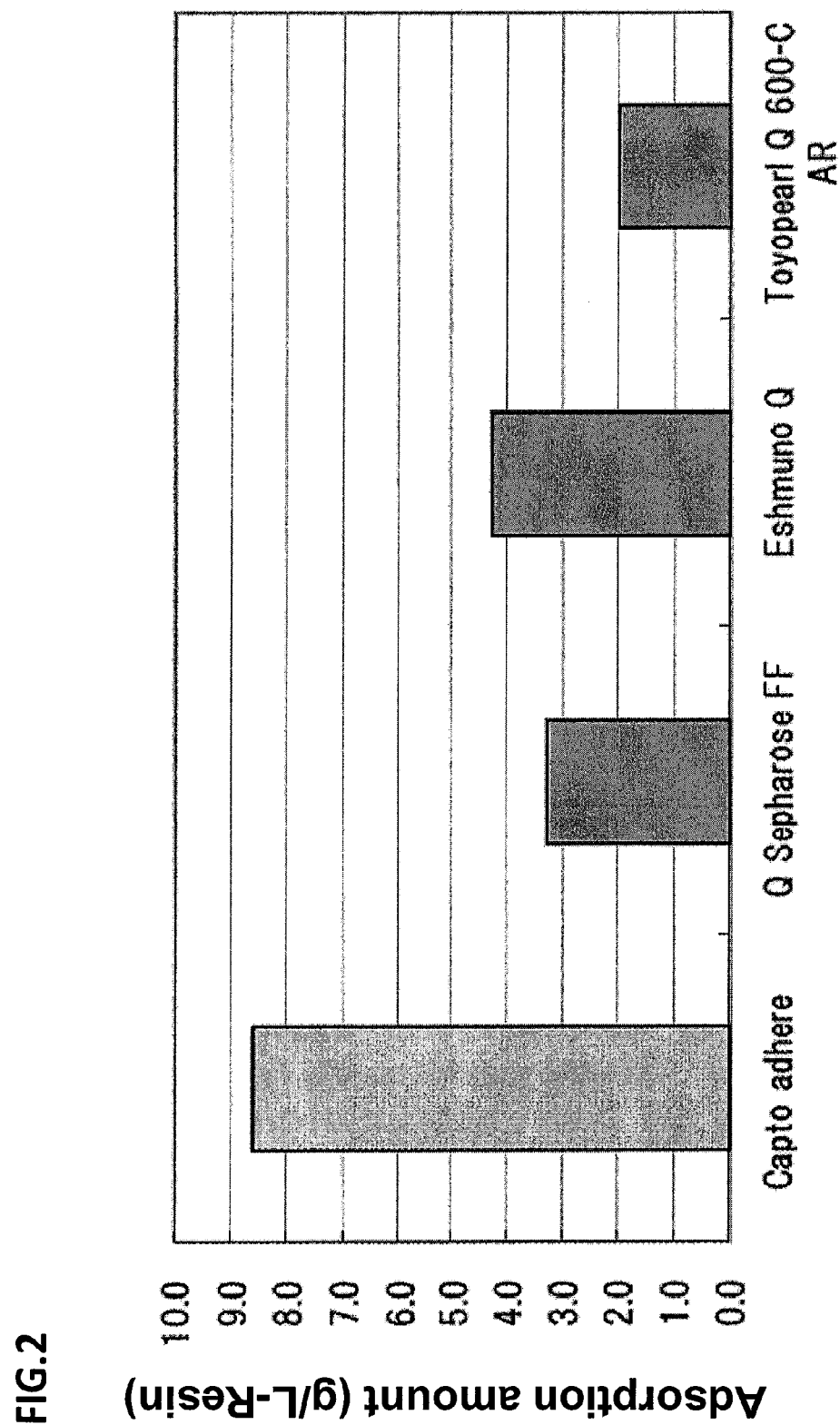
FIG. 2 shows the adsorption amount of Antithrombin per 1 mL of carrier.

As shown in FIG. 2, the mixed mode carrier, Capto adhere showed much higher adsorption amount than other anion exchange carriers.

These results showed that the anion exchange carrier showed the adsorption amount of Antithrombin in the culture fluid being half or lower than that of the mixed mode carrier. That is, the adsorption amount of Antithrombin onto the anion exchange carrier is remarkably low, and thus the anion exchange carrier is not suitable to be directly used for industrial-scale purification from the culture fluid.

Example 6

A Method for Directly Recovering Protein S from the Culture Supernatant Using the Mixed Mode Carrier and a Difference in the Yield Between the Mixed Mode Carrier and Anion Exchange Carrier The CHO cell culture supernatant containing 20.0 mg of Protein S (pH was adjusted to 5.0 and precipitates were removed by centrifugation) was directly passed through the mixed mode column (manufactured by GE Healthcare, Capto MMC, column volume: 3.9 mL) equilibrated with buffer PA (20 mmol/L sodium phosphate, 10 mmol/L sodium citrate buffer, pH 5.0) so as to adsorb Protein S thereto.

The column was washed with 19.6 mL of buffer PA, and then 39.3 mL of buffer PB (20 mmol/L sodium phosphate, 10 mmol/L sodium citrate buffer, pH 7.0) was applied thereto to elute Protein S.

Thereafter, 19.6 mL of solution PC (20 mmol/L sodium phosphate, 10 mmol/L sodium citrate, 500 mmol/L sodium chloride solution, pH 7.0) was applied thereto to elute Protein S remaining in the column [this is referred to as Purification (1)].

The CHO cell culture supernatant containing 84.9 mg of Protein S was directly passed through the mixed mode column (manufactured by GE Healthcare, Capto MMC, column volume: 3.9 mL) equilibrated with buffer PA to adsorb Protein S thereto.

The column was washed with 24.9 mL of buffer PA, and then 39.3 mL of buffer PB was applied thereto to elute Protein S. Thereafter, 20.1 mL of solution PC (20 mmol/L sodium phosphate, 10 mmol/L sodium citrate, 500 mmol/L sodium chloride solution, pH 7.0) was applied to elute Protein S remaining in the column [this is referred to as Purification (2)].

The CHO cell culture supernatant containing 20.0 mg of Protein S was directly passed through the cation exchange column (manufactured by Merck Millipore, Fractogel SE Hicap, column volume: 3.9 mL) equilibrated with buffer PA (20 mmol/L sodium phosphate, 10 mmol/L sodium citrate buffer, pH 5.0) to adsorb Protein S thereto.

The column was washed with 24.1 mL of buffer PA, and then 39.3 mL of buffer PB (20 mmol/L sodium phosphate, 10 mmol/L sodium citrate buffer, pH 7.0) was applied thereto to elute Protein S.

Thereafter, 19.6 mL of solution PC (20 mmol/L sodium phosphate, 10 mmol/L sodium citrate, 500 mmol/L sodium chloride solution, pH 7.0) was applied to elute Protein S remaining in the column [this is referred to as Purification (3)].

The CHO cell culture supernatant containing 8 to 10 mg of Protein S was directly passed through the anion exchange column (manufactured by GE Healthcare, Q Sepharose XL, column volume: 0.98 mL) equilibrated with buffer PG (20 mmol/L Tris hydrochloride, 150 mmol/L sodium chloride solution, pH7.4) to adsorb Protein S thereto.

The column was washed with 7.9 mL of buffer PG, and then 7.9 mL of buffer PH (20 mmol/L Tris hydrochloride, 200 mmol/L sodium chloride solution, pH 7.4) was applied thereto to elute Protein S. Thereafter, 7.9 mL of buffer PI (20 mmol/L Tris hydrochloride, 1 mol/L sodium chloride solution, pH 7.4) was applied to elute Protein S remaining in the column [this is referred to as Purification (4)].

The CHO cell culture supernatant containing 8 to 10 mg of Protein S was directly passed through the anion exchange column (manufactured by GE Healthcare, Capto Q, column volume: 0.98 mL) equilibrated with buffer PG to adsorb Protein S thereto.

The column was washed with 7.9 mL of buffer PG, and then 7.9 mL of buffer PH was applied thereto to elute Protein S. Thereafter, 7.9 mL of buffer PI was applied to elute Protein S remaining in the column [this is referred to as Purification (5)].

The culture supernatant of Protein S, and the Protein S in the wash solutions before elution and in eluates in Purification (1) to (5) were measured by reversed-phase HPLC method [J. Chromatography B, 662, 209(1994)], and the recovery was calculated. The results are shown in Table 2.

TABLE 2

| Protein S yield in eluted fraction of each carrier | | | | | |
|---|---|---|---|---|---|
| | Purification (1) | Purification (2) | Purification (3) | Purification (4) | Purification (5) |
| Chromatography carrier | Capto MMC | Capto MMC | Fractogel SE Hicap (M) | Q Sepharose XL | Capto Q |

TABLE 2-continued

Protein S yield in eluted fraction of each carrier

|  | Purification (1) | Purification (2) | Purification (3) | Purification (4) | Purification (5) |
|---|---|---|---|---|---|
| Adsorption amount per 1 mL of carrier (mg) | 5.1 | 21.6 | 5.1 | 8 to 10 | 8 to 10 |
| Yield in eluted fraction (%) | 91.9 | 85.7 | 21.6 | 24.1 | 13.1 |

As shown in Table 2, the process yield of Protein S in the mixed mode carrier was as good as 80% irrespective of loading amount. In contrast, whreas the adsorption amount per 1 mL of other carrier was as low as 10 mg or less, the recovery was as remarkably low as 25% or less.

These results suggest that the adsorption amount of Protein S onto the ion exchange carrier was very low, and thus the ion exchange carrier is not suitable for industrial-scale use when directly purifying Protein S directly from the culture fluid.

Example 7

Removal of Protein S Aggregates in Purification of Protein S from the Culture Supernatant Using the Mixed Mode Carrier pH of the CHO cell culture supernatant containing 84.4 mg of Protein S was adjusted to 5.0, and precipitates were removed by centrifugation. This solution was directly passed through the mixed mode column (manufactured by GE Healthcare, Capto MMC, column volume: 3.9 mL) equilibrated with buffer PJ (50 mmol/L acetic acid, pH 5.3) to adsorb Protein S thereto.

The column was washed with 19.6 mL of buffer PJ, and then 36.9 mL of buffer PK (200 mmol/L sodium phosphate, pH 7.0) was applied to elute Protein S. Thereafter, 19.6 mL of solution PL (1 mol/L sodium chloride solution) was applied thereto to elute Protein S remaining in the column. The results are shown in FIG. 3.

The presence or absence of the Protein S aggregate in the eluted fraction was analyzed by Native-Western Blotting. Each fraction was loaded onto a 4-12% Tris-Glycine Gel (manufactured by Invitrogen) so that the amount of protein of Protein S is 1 µg, followed by electrophoresis. Thereafter, the protein was transferred onto a PVDF membrane, and Protein S was labeled with primary and secondary antibodies. Band images of Protein S were obtained by HRP color development. The results are shown in FIG. 4.

Figure 3:
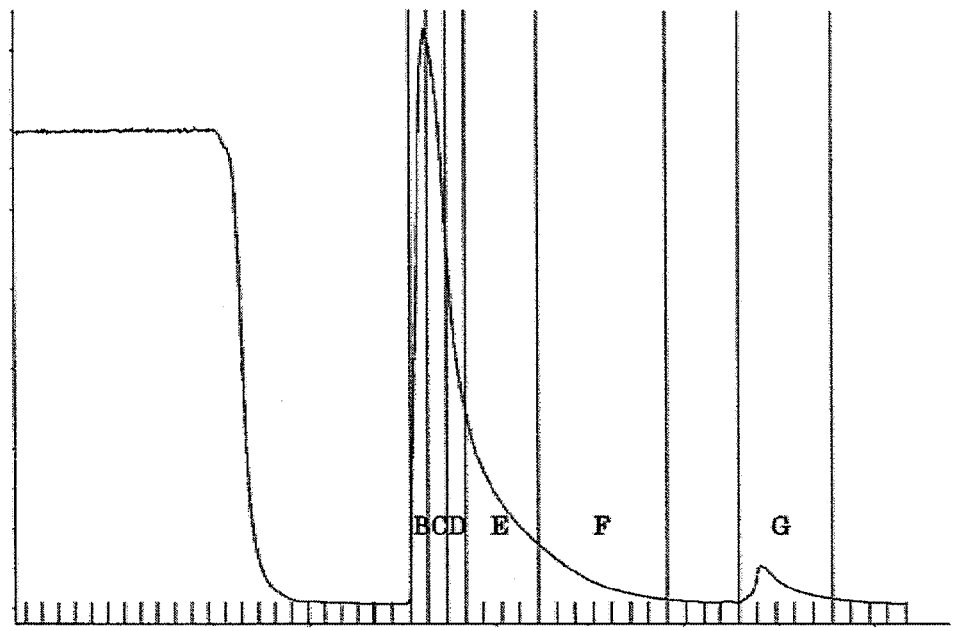
FIG. 3 shows a chromatogram in the purification of Protein S culture supernatant using the mixed mode carrier of Example 7, in which B to E represent the desired fractions of Protein S, and G represents a fraction mainly containing aggregates. A vertical axis represents absorbance at UV 280 nm, and a horizontal axis represents elution time.
Figure 4:
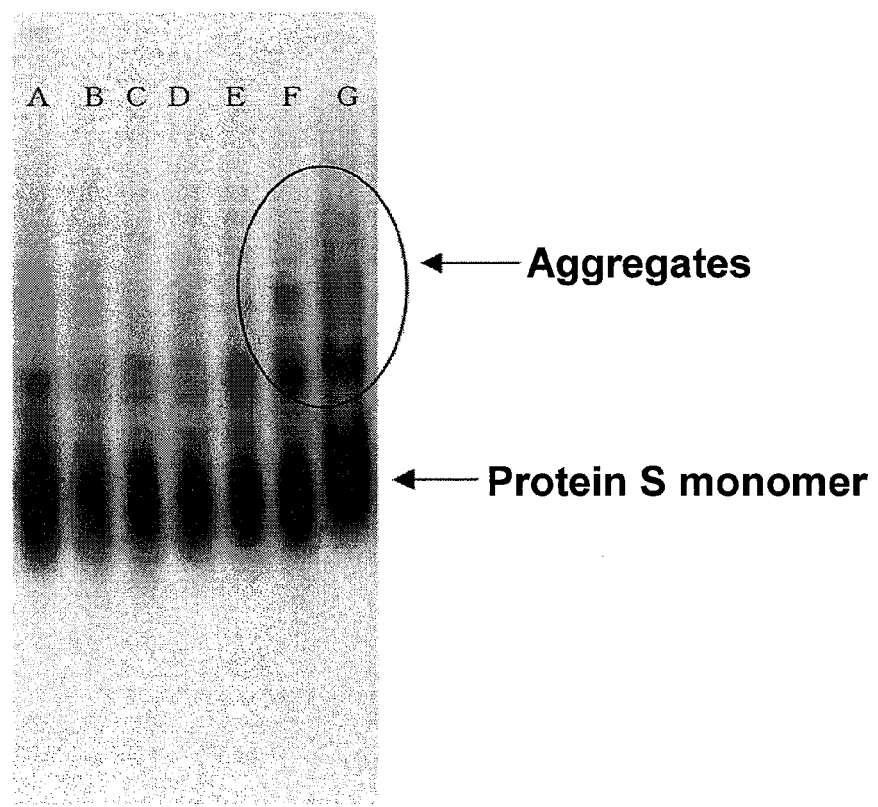
FIG. 4 shows Native-Western Blotting analysis regarding the presence and absence of aggregates in the eluted fractions, in which A represents the culture supernatant added, and B to G represent the eluted fractions in the purification using the mixed mode carrier and correspond to B to G of FIG. 3. The lowest and strongest band represents Protein S monomers.

As a result, as shown in FIGS. 3 and 4, the fractions containing Protein S with the desired quality were determined as B to E. The recovery of Protein S included in this range of eluate was 84%, and the content of the aggregate was also low.

As described above, the culture supernatant was directly applied to the mixed mode carrier, Protein S was adsorbed onto the carrier, the washing process was carried out, proper pH and salt concentration conditions were selected, Protein S was eluted, and the elution range was selected, thereby obtaining a fraction from which Protein S aggregates are successfully removed.

Example 8

Differences in Purity and Aggregate Fractionation Ability Between the Mixed Mode Carrier and the Hydrophobic Chromatography Carrier in the Purification of Protein S from the Culture Supernatant pH of the CHO cell culture supernatant containing 9.9 mg of Protein S was adjusted to 5.0 using phosphate, and precipitates were removed by centrifugation. This solution was directly passed through the mixed mode column (manufactured by GE Healthcare, Capto MMC, column volume: 0.98 mL) equilibrated with buffer PM (20 mmol/L sodium phosphate buffer, pH 5.0) to adsorb Protein S thereto.

Figure 5:
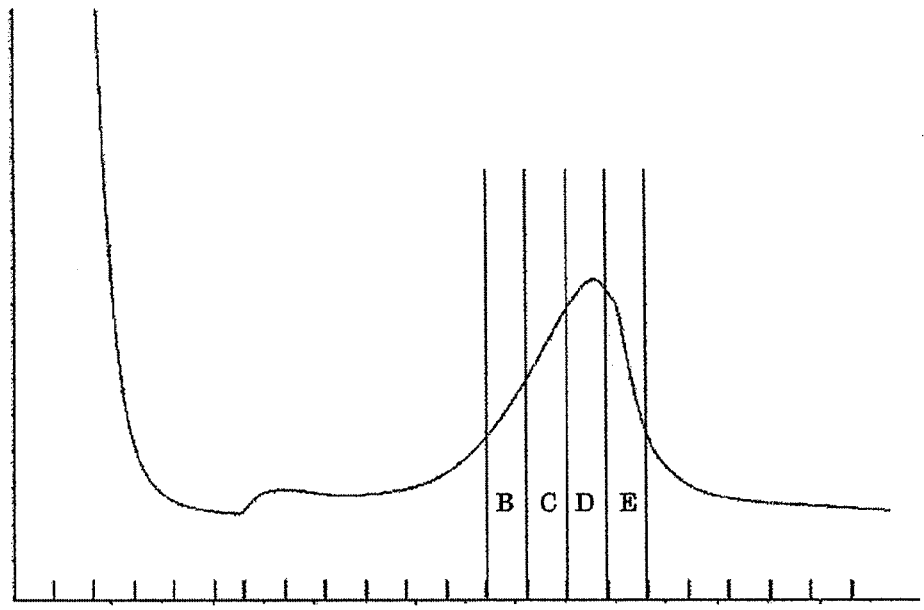
FIG. 5 shows a chromatogram in the purification of Protein S culture supernatant using the mixed mode carrier of Example 8, in which B to E represent elution peaks when purification was performed using Capto MMC carrier. A vertical axis represents absorbance at UV 280 nm, and a horizontal axis represents elution time.

The column was washed with 9.8 mL of buffer PM, and then buffer PN (20 mmol/L Tris hydrochloride, pH 7.0) was applied to elute Protein S [this is referred to as Purification (6)]. Fraction patterns of elution peak of Purification (6) are shown in FIG. 5.

A solution PO (sodium chloride in saturated sodium citrate solution) was added to the CHO cell culture supernatant containing 10.7 mg of Protein S to be 30% of the total volume (pretreatment), and precipitates were removed by centrifugation.

Figure 6:
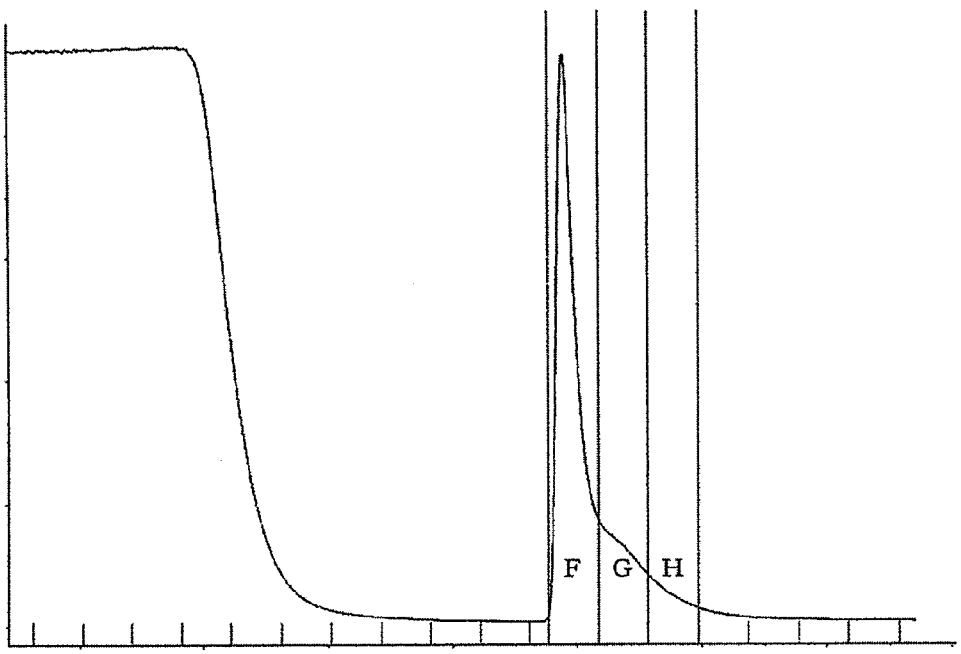
FIG. 6 shows a chromatogram in the purification of Protein S culture supernatant using the hydrophobic mode carrier of Example 8, in which F to H represent elution peaks when column purification was performed using Phenyl Sepharose 6 FF (high sub) carrier. A vertical axis represents absorbance at UV 280 nm, and a horizontal axis represents elution time.

This solution was directly passed through the hydrophobic chromatography column (manufactured by GE Healthcare, Phenyl Sepharose 6 FF, 0.98 mL) equilibrated with solution PP (3-fold dilution of solution PO with ultrapure water) to adsorb Protein S thereto. The column was washed with 15.5 mL of solution PP, and then purified water was applied to elute Protein S [this is referred to as Purification (7)]. Fraction patterns of elution peak of Purification (7) are shown in FIG. 6. In contrast, when the culture supernatant of Protein S was directly applied to a hydrophobic mode carrier, Protein S was not adsorbed thereto.

SDS-PAGE analysis was performed using fractions of the main peak regions of Purifications (6) and (7). Each fraction was applied to a 4-20% Tris-Glycine Gel (manufactured by Invitrogen) so that the amount of protein of Protein S is 2.5 µg, followed by electrophoresis and CBB staining. The results are shown in FIG. 7.

Figure 7:
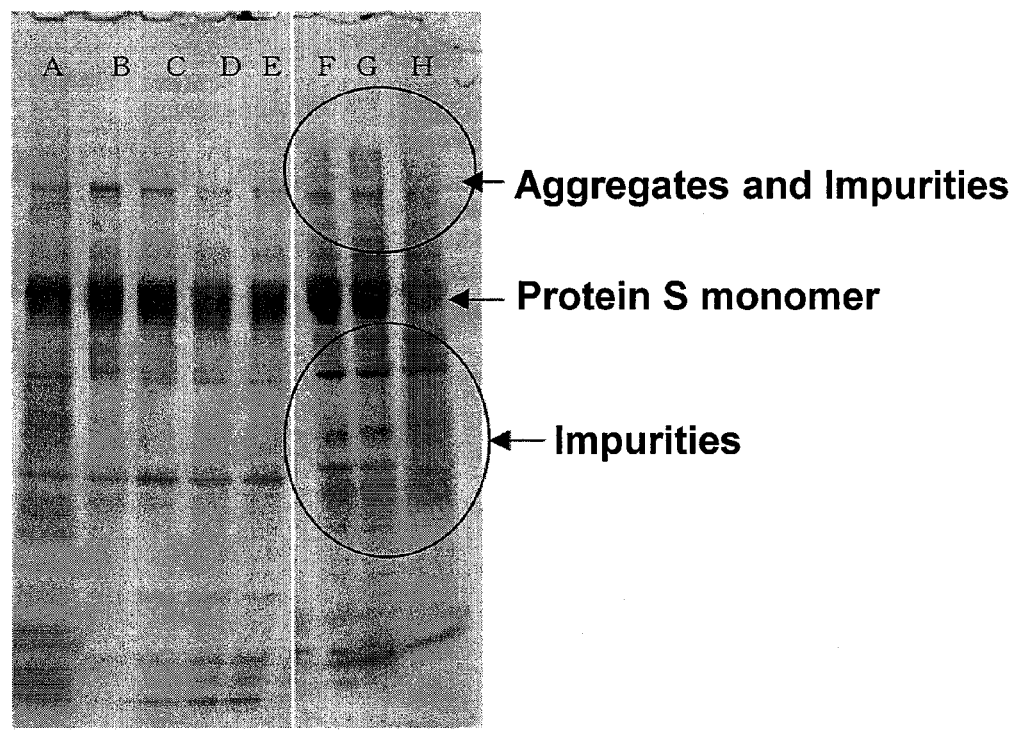
FIG. 7 shows SDS-PAGE analysis of fraction solutions in the purification using the mixed mode carrier and the hydrophobic mode carrier, in which A represents the culture supernatant loaded onto the column, B to E represent the fraction solutions of the chromatogram shown in FIG. 5, and F to H represent the fraction solutions of the chromatogram shown in FIG. 6.

As shown in FIG. 7, the eluate obtained by Purification (6) was found to have higher Protein S purity than the eluate obtained by Purification (7). Further, in Purification (6), no bands were detected in higher molecular weight region than the bands of Protein S, indicating that purification by the mixed mode carrier is more excellent in term of the aggregate removal than purification by hydrophobic chromatography.

Example 9

Example of Controlling the Number of Bound Sialic Acids of Antithrombin Using the Mixed Mode Carrier (Example of a Method for More Increasing the Number of Bound Sialic Acids Using a Glycine Buffer)

A CHO cell culture supernatant containing 428 mg of Antithrombin was directly passed through the mixed mode column (manufactured by GE Healthcare, Capto adhere, column volume: 28.5 mL) equilibrated with buffer AC (300 mmol/L glycine, 100 mmol/L sodium chloride, 20 mmol/L sodium phosphate buffer, pH 6.0) to adsorb Antithrombin thereto.

The column was washed with 228 mL of buffer AC containing glycine (300 mmol/L glycine, 100 mmol/L sodium chloride, 20 mmol/L sodium phosphate buffer, pH 6.0), and then 143 mL of buffer AB (350 mmol/L sodium chloride, 20 mmol/L sodium phosphate buffer, pH 7.0) was applied to elute Antithrombin. The number of bound sialic acids of Antithrombin recovered in the particular range of fractions after elution was measured in the same manner as in Example 1.

As a result, when purification was performed under the conditions of Example 9 (buffer AC used for equilibration and washing before elution), the number of bound sialic acids (quality of Antithrombin) was increased to 1.3-fold, compared to the purification conditions of Example 1 (buffer AA used for equilibration and washing before elution). It can be seen that quality (number of bound sialic acids) of Antithrombin eluted can be more improved by addition of glycine to the buffer used for washing before elution.

Example 10

A Method for Directly Recovering Protein S from the Culture Supernatant Using the Mixed Mode Carrier and a Difference in the Yield Between the Mixed Mode Carrier and Anion Exchange Carrier The CHO cell culture supernatant containing 19.9 mg of Protein S (pH was adjusted to 5.0 and precipitates were removed by centrifugation) was directly passed through the mixed mode column (manufactured by GE Healthcare, Capto MMC, column volume: 3.9 mL) equilibrated with buffer PA (20 mmol/L sodium phosphate, 10 mmol/L sodium citrate buffer, pH 5.0) to adsorb Protein S thereto.

The column was washed with 19.6 mL of buffer PA, and then 41.9 mL of buffer PB (20 mmol/L sodium phosphate, 10 mmol/L sodium citrate buffer, pH 7.0) was applied thereto to elute Protein S. Thereafter, 19.6 mL of buffer PC (20 mmol/L sodium phosphate, 10 mmol/L sodium citrate, 500 mmol/L sodium chloride solution, pH 7.0) was applied thereto to elute Protein S remaining in the column [this is referred to as Purification (1)].

The CHO cell culture supernatant containing 87.7 mg of Protein S was directly passed through the mixed mode column (manufactured by GE Healthcare, Capto MMC, column volume: 3.9 mL) equilibrated with buffer PA to adsorb Protein S thereto. The column was washed with 24.9 mL of buffer PD (50 mmol/L sodium phosphate, 25 mmol/L sodium citrate buffer, pH 5.0), and then 39.3 mL of buffer PE (50 mmol/L sodium phosphate, 25 mmol/L sodium citrate buffer, pH 7.0) was applied thereto to elute Protein S.

Thereafter, 20.1 mL of buffer PP (50 mmol/L sodium phosphate, 25 mmol/L sodium citrate, 500 mmol/L sodium chloride solution, pH 7.0) was applied to elute Protein S remaining in the column [this is referred to as Purification (2)].

The CHO cell culture supernatant containing 21.8 mg of Protein S was directly passed through the cation exchange column (manufactured by Merck Millipore, Fractogel SE Hicap, column volume: 3.9 mL) equilibrated with buffer PA (20 mmol/L sodium phosphate, 10 mmol/L sodium citrate buffer, pH 5.0) to adsorb Protein S thereto.

The column was washed with 18.3 mL of buffer PA, and then 39.3 mL of buffer PB (20 mmol/L sodium phosphate, 10 mmol/L sodium citrate buffer, pH 7.0) was applied thereto to elute Protein S. Thereafter, 19.6 mL of buffer PC (20 mmol/L sodium phosphate, 10 mmol/L sodium citrate, 500 mmol/L sodium chloride solution, pH 7.0) was applied to elute Protein S remaining in the column [this is referred to as Purification (3)].

The CHO cell culture supernatant containing 8 to 10 mg of Protein S was directly passed through the anion exchange column (manufactured by GE Healthcare, Q Sepharose XL, column volume: 0.98 mL) equilibrated with buffer PG (20 mmol/L Tris hydrochloride, 150 mmol/L sodium chloride solution, pH 7.4) to adsorb Protein S thereto.

The column was washed with 7.9 mL of buffer PG, and then 7.9 mL of buffer PH (20 mmol/L Tris hydrochloride, 200 mmol/L sodium chloride solution, pH 7.4) was applied thereto to elute Protein S. Thereafter, 7.9 mL of buffer PI (20 mmol/L Tris hydrochloride, 1 mol/L sodium chloride solution, pH 7.4) was applied to elute Protein S remaining in the column [this is referred to as Purification (4)].

The CHO cell culture supernatant containing 8 to 10 mg of Protein S was directly passed through the anion exchange column (manufactured by GE Healthcare, Capto Q, column volume: 0.98 mL) equilibrated with buffer PG to adsorb Protein S thereto. The column was washed with 7.9 mL of buffer PG, and then 7.9 mL of buffer PH was applied thereto to elute Protein S. Thereafter, 7.9 mL of buffer PT was applied to elute Protein S remaining in the column [this is referred to as Purification (5)].

The culture supernatant of Protein S, and the Protein S in the wash solutions before elution and in eluates in Purification (1) to (5) were measured by reversed-phase HPLC method [J. Chromatography B, 662, 209 (1994)], and the recovery was calculated. The results are shown in Table 3.

TABLE 3

| Protein S yield in eluted fraction of each carrier | | | | | |
|---|---|---|---|---|---|
| | Purification (1) | Purification (2) | Purification (3) | Purification (4) | Purification (5) |
| Chromatography carrier | Capto MMC | Capto MMC | Fractogel SE Hicap (M) | Q Sepharose XL | Capto Q |
| Adsorption amount per 1 mL of carrier (mg) | 5.1 | 22.3 | 5.6 | 8 to 10 | 8 to 10 |
| Yield in eluted fraction (%) | 91.9 | 85.8 | 21.7 | 24.1 | 13.1 |

As shown in Table 3, the process yield of Protein S in the mixed mode carrier was as good as 80% or more irrespective of loading amount. In contrast, whereas the adsorption amount per 1 mL of other carrier was as low as 10 mg or less, the recovery was as remarkably low as 25% or less.

These results suggest that the adsorption amount of Protein S onto the ion exchange carrier was very low, and thus the ion exchange carrier is not suitable for industrial-scale use when purifying Protein S directly from the culture fluid.

Example 11

A Method for Directly Recovering Erythropoietin from the Culture Supernatant Using the Mixed Mode Carrier The CHO cell culture supernatant containing 118 mg of Erythropoietin was directly passed through the mixed mode column (manufactured by GE Healthcare, Capto adhere, column volume: 5.9 mL) equilibrated with buffer EA (10 mmol/L Tris buffer, pH 6.4) to adsorb Erythropoietin thereto.

The column was washed with 29.5 mL of buffer EA (10 mmol/L Tris buffer, pH 6.4), and then Erythropoietin was eluted with a linear gradient of sodium chloride using 29.5 mL of buffer EA (10 mmol/L Tris buffer, pH 6.4) and buffer EB (500 mmol/L sodium chloride, 10 mmol/L Tris buffer, pH 6.4).

The Erythropoietin concentrations in the washing fraction before elution and in a particular range of eluate were measured by surface plasmon resonance (Biacore3000, manufactured by GE Healthcare) using an anti-Erythropoietin antibody-immobilized sensor chip.

As a result, the adsorption amount of Erythropoietin per unit carrier volume (1 L) was 3 g. Therefore, it can be seen that Erythropoietin can be directly recovered from the culture supernatant using the mixed mode carrier.

Example 12

Inhibition of Neuraminidase and Protease Activities by Addition of Amino Acids (Protein S-Containing Aqueous Solution)

The CHO cell culture supernatant containing 299 mg of Protein S (pH was adjusted to 5.0 and precipitates were removed by centrifugation) was directly passed through the mixed mode column (manufactured by GE Healthcare, Capto MMC, column volume: 32.8 mL) equilibrated with buffer PQ (50 mmol/L acetic acid solution, pH 5.0) to adsorb Protein S thereto.

The column was washed with 164 mL of buffer PQ (50 mmol/L acetic acid solution, pH 5.0), and then 262.4 mL of buffer PR (100 mmol/L sodium phosphate solution, pH 7.0) was applied to elute Protein S.

Neuraminidase (manufactured by Nacalai Tesque) was added to the aqueous solution containing Protein S at a final concentration of 0.0005 U/mL. As a control group, purified water was added in the same amount as the neuraminidase. Glycine was added at a final concentration of 1.0 mol/L, or purified water as a control, and held at 37° C. for 3 hours.

The solvent of the product was replaced with purified water, and then isoelectric focusing electrophoresis (pH3-7 IEF Gel, manufactured by Invitrogen, loading amount of protein of Protein S: 10 μg) was performed for analysis. The results are shown in FIG. 8.

Figure 8:
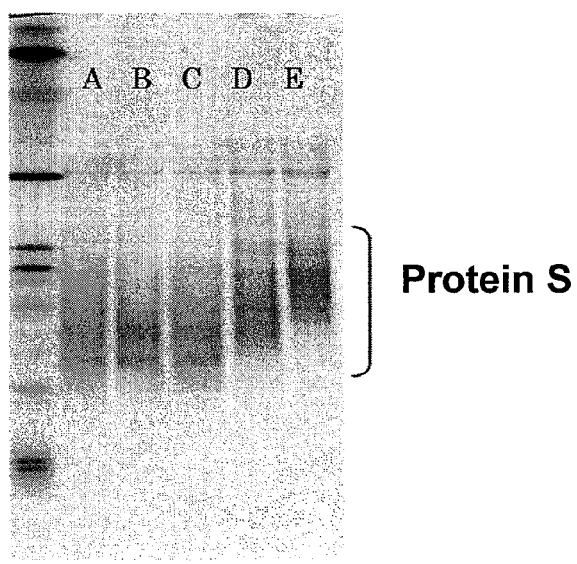
FIG. 8 shows the results of isoelectric focusing electrophoresis of the aqueous solution containing Protein S, which was added with neuraminidase and amino acids, in which A represents a sample that was frozen and stored immediately after addition of purified water to the aqueous solution containing Protein S, B represents a sample that was held at 37° C. for 3 hours after addition of purified water to the aqueous solution containing Protein S, C represents a sample that was held at 37° C. for 3 hours after addition of glycine (final concentration of 1.0 mol/L) and purified water to the aqueous solution containing Protein S, D represents a sample that was held at 37° C. for 3 hours after addition of glycine (final concentration of 1.0 mol/L) and neuraminidase (final concentration of 0.0005 U/mL) to the aqueous solution containing Protein S, and E represents a sample that was held at 37° C. for 3 hours after addition of neuraminidase (final concentration of 0.0005 U/mL) and purified water to the aqueous solution containing proteins. The upper side of electrophoretic profile indicates a basic side and the lower side thereof indicates an acidic side.

As shown in FIG. 8, electrophoretic profile of the aqueous solution containing Protein S where purified water was added showed a basic shift. In contrast, electrophoretic profile of the aqueous solution containing Protein S where glycine was added showed a basic shift compared to electrophoretic profile before initiation, but major bands were found in a more acidic region than the band of purified water-added one.

These results suggest that neuraminidase activity is inhibited by addition of amino acids to maintain quality (number of bound sialic acids) of Protein S.

Similarly, glycine (final concentration of 0.5 mol/L), arginine (final concentration of 0.4 mol/L) or purified water was added to the aqueous solution containing Protein S that was obtained in the chromatographic process using the mixed mode carrier described in 6 above, respectively and held at 25° C. or 4° C. for 6 days. SDS-PAGE method (4-20% Tris-Glycine Gel, manufactured by Invitrogen, loading amount of protein of Protein S: 2.4 μg) was performed for analysis. The results are shown in FIG. 9.

Figure 9:
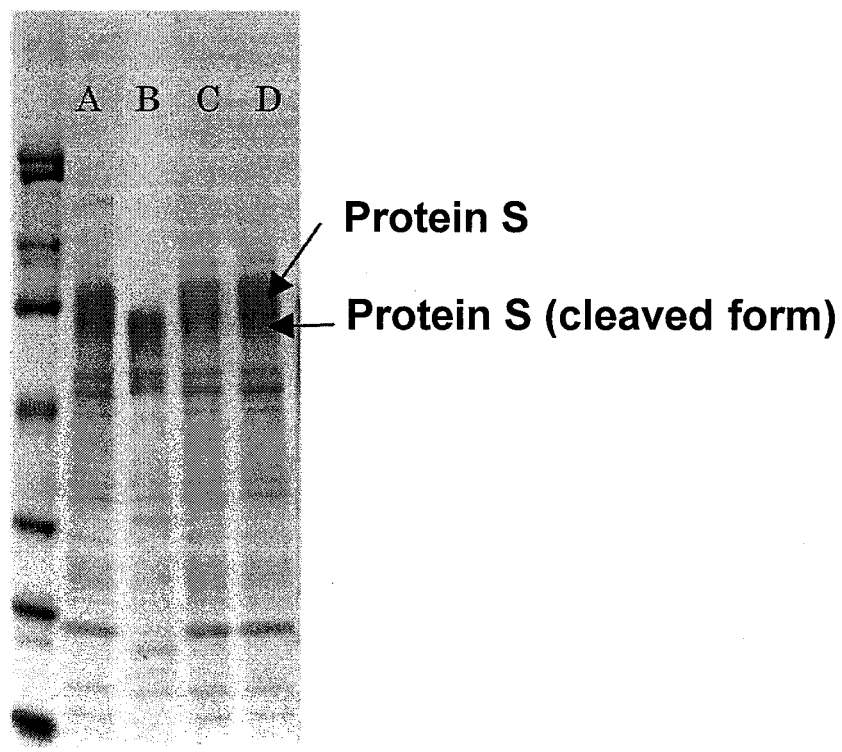
FIG. 9 shows the results of SDS-PAGE of the aqueous solution containing Protein S, which was added with amino acids and held at 25° C. for 6 days, in which A represents a sample that was held at 4° C. for 6 days after addition of purified water to the aqueous solution containing Protein S, B represents a sample that was held at 25° C. for 6 days after addition of purified water to the aqueous solution containing Protein S, C represents a sample that was held at 25° C. for 6 days after addition of glycine (final concentration of 0.5 mol/L) to the aqueous solution containing Protein S, and D represents a sample that was held at 25° C. for 6 days after addition of arginine (final concentration of 0.4 mol/L) to the aqueous solution containing Protein S.

As shown in FIG. 9, it was found that Protein S was completely converted into the cleaved form in the sample added with purified water whereas conversion of Protein S into the cleaved form was inhibited in the samples added with glycine and arginine. These results suggest that protease activity is inhibited by addition of amino acids, thereby inhibiting formation of the cleaved form of Protein S.

Example 13

Inhibition of Neuraminidase Activity by Addition of Amino Acids (Erythropoietin-Containing Aqueous Solution)

Purified water, 1 mol/L alanine solution, 1 mol/L arginine solution, or 1 mol/L glycine solution was mixed with the culture fluid containing Erythropoietin in an equivalent amount, respectively and then held at 25° C. for 7 days. Thereafter, Erythropoietin was purified using an anti-Erythropoietin antibody-immobilized affinity chromatography column, and the number of sialic acids binding to Erythropoietin was measured by capillary electrophoresis [Biol. Pharm. Bull. 33(9) 1596-1599 (2010)]. The results are shown in FIG. 10.

Figure 10:
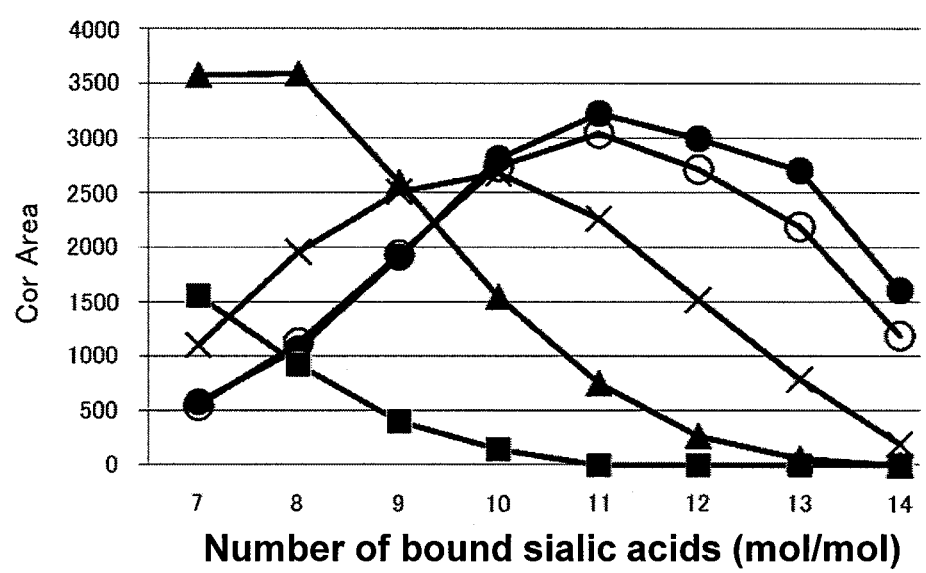
FIG. 10 shows the results of capillary electrophoresis of Erythropoietin purified from the culture fluid containing Erythropoietin, which was added with amino acids and held at 25° C. for 7 days. A vertical axis represents peak area, and a horizontal axis represents the number of bound sialic acids (mol/mol). Closed circle indicates a sample upon initiation of measurement, closed square indicates a sample which was added with purified water and held at 25° C. for 7 days, closed triangle indicates a sample which was added with 1 mol/L alanine and held at 25° C. for 7 days, cross indicates a sample which was added with 1 mol/L glycine and held at 25° C. for 7 days, and opened circle indicates a sample which was added with 1 mol/L arginine and held at 25° C. for 7 days.

As shown in FIG. 10, the component showing the relatively high number of bound sialic acids disappeared in the solution added with purified water, whereas the number of bound sialic acids was maintained in the solution added with amino acids, compared to the solution added with purified water. The effect was strong in this order: arginine, glycine, and alanine. Under the arginine-added conditions, in particular, the number of bound sialic acids was equivalent, compared to that at initiation of incubation. These results suggest that neuraminidase activity in the Erythropoietin aqueous solution is inhibited by addition of amino acids.

Example 14

Example of Purification of Antithrombin α Form by Combination of Addition of Amino Acids and Other Chromatography Several-fold dilution of the CHO cell culture supernatant containing 5.79 g of Antithrombin was performed using purified water, and then passed through the column (manufactured by Merck, Eshmuno Q, column volume: 456 mL) equilibrated with buffer AR (300 mmol/L glycine, 20 mmol/L sodium phosphate buffer, pH 7.0) to adsorb Antithrombin thereto.

The column was washed with 6 column volumes of buffer AR (300 mmol/L glycine, 20 mmol/L sodium phosphate buffer, pH 7.0), and then 4 column volumes of buffer AS (350 mmol/L sodium chloride, 20 mmol/L sodium phosphate buffer, pH 6.0) was applied to elute Antithrombin. 954 mL of the recovered liquid was obtained. pH of this recovered liquid was adjusted to 7.0 using buffer AT (250 mmol/L glycine buffer, pH 10.0). The recovery of Antithrombin in this process was as good as 95%.

The aqueous solution containing Antithrombin thus recovered in the above mentioned process was mixed with Triton X-100 and tributyl phosphate at their concentrations of 1% and 0.3%, respectively, followed by gently stirring. Several-fold dilution of this solution was carried out using purified water, and the solution was passed through the column (manufactured by Merck, Eshmuno Q, column volume: 209 mL) equilibrated with buffer AE (20 mmol/L sodium phosphate buffer, pH 7.0) to adsorb Antithrombin thereto.

The column was washed with 3 column volumes of buffer AE (20 mmol/L sodium phosphate buffer, pH 7.0), and then 4 column volumes of buffer AS (350 mmol/L sodium chloride, 20 mmol/L sodium phosphate buffer, pH 6.0) was applied to elute Antithrombin. pH of this recovered liquid was adjusted to 7.0 with buffer AT (250 mmol/L glycine buffer, pH 10.0). The recovery of Antithrombin in this process was as good as 100%.

Sodium phosphate buffer or purified water was added to the aqueous solution containing Antithrombin thus recovered in the above mentioned process, and pH and conductivity were adjusted to 6.0 and 24.1 mS/cm, respectively. This solution was passed through the column (manufactured by JNC, Cellufine Sulfate, column volume: 530 mL) equilibrated with buffer AU (160 mmol/L sodium chloride, 20 mmol/L sodium phosphate buffer, pH 6.0) to recover and neutralize a solution that was passed through the column.

Several-fold dilution of the aqueous solution containing Antithrombin recovered in the above mentioned process was carried out with buffer AG (1.5 mol/L sodium citrate, 20 mmol/L sodium phosphate buffer, pH 7.0). This solution was passed through the column (manufactured by GE Healthcare, Phenyl Sepharose 6 Fast Flow, column volume: 177 mL) equilibrated with buffer AH (1 mol/L sodium citrate, 20 mmol/L sodium phosphate buffer, pH 8.0) to adsorb Antithrombin thereto.

The column was washed with 2 column volumes of buffer AH (1 mol/L sodium citrate, 20 mmol/L sodium phosphate buffer, pH 8.0), and then Antithrombin was eluted with a linear gradient of sodium citrate.

The aqueous solution containing Antithrombin thus recovered in the above mentioned process was concentrated by the ultrafiltration membrane (manufactured by Merck, a molecular weight cut off: 10 kilodaltons) to a proper concentration, followed by the exchange with buffer AI (20 g/L glycine, 12 g/L sodium citrate buffer, pH 7.5), thereby obtaining an aqueous solution containing the purified Antithrombin α form.

The number of bound sialic acids of this solution was measured in the same manner as in Example 1. As a result, the number of bound sialic acids was 6.6 mol/mol and the binding ratio of sialic acid was 83%.

Example 15

Example of Purification of Antithrombin α Form by Combination of Mixed Mode Carrier and Other Chromatography A CHO cell culture supernatant containing 3.14 g of Antithrombin was purified in the same manner as in Example 2 (except that buffer AD (450 mmol/L sodium chloride, 20 mmol/L sodium phosphate buffer, pH 6.0) was used instead of buffer AC, and the column volume was 114 mL), and the particular range of fractions were recovered, thereby obtaining 706 mL of the recovered liquid. The recovery of Antithrombin in this process was as good as 89%.

The aqueous solution containing Antithrombin thus recovered in the above mentioned process was mixed with TritonX-100 and tributyl phosphate at their concentrations of 1% and 0.3%, respectively, followed by gently stirring. This solution was diluted several-fold with purified water, and then it was passed through the column (manufactured by Merck, Eshmuno Q, column volume 28.5 mL) equilibrated with buffer AE (20 mmol/L sodium phosphate buffer, pH 7.0) to adsorb Antithrombin thereto.

The column was washed with 3 column volumes of buffer AE (20 mmol/L sodium phosphate buffer, pH 7.0), and then 4 column volumes of buffer AB (350 mmol/L sodium chloride, 20 mmol/L sodium phosphate buffer, pH 7.0) was applied to elute Antithrombin.

Sodium phosphate buffer or purified water was added to the aqueous solution containing Antithrombin recovered in the above mentioned process, and pH and conductivity were adjusted to 6.0 and 34.8 mS/cm, respectively. This solution was passed through the column (manufactured by GE Healthcare, Capto DeVirS, column volume: 23.7 mL) equilibrated with buffer AF (170 mmol/L sodium chloride, 20 mmol/L sodium phosphate buffer, pH 6.0) to recover and neutralize a solution that was passed through the column.

Several-fold dilution of the aqueous solution containing Antithrombin thus recovered in the above mentioned process was carried out with buffer AG (1.5 mol/L sodium citrate, 20 mmol/L sodium phosphate buffer, pH 7.0). This solution was passed through the column (manufactured by GE Healthcare, Phenyl Sepharose 6 Fast Flow, column volume: 23.7 mL) equilibrated with buffer AH (1 mol/L sodium citrate, 20 mmol/L sodium phosphate buffer, pH 8.0) to adsorb Antithrombin thereto.

The column was washed with 2 column volumes of buffer AH (1 mol/L sodium citrate, 20 mmol/L sodium phosphate buffer, pH 8.0), and then Antithrombin was eluted with a linear gradient of sodium citrate.

The aqueous solution containing Antithrombin recovered in the above mentioned process was concentrated by the ultrafiltration membrane (manufactured by Merck, a molecular weight cut off: 10 kilodaltons) to a proper concentration, followed by the exchange with buffer AI (20 g/L glycine, 12 g/L sodium citrate buffer, pH 7.5), thereby obtaining an aqueous solution containing the purified Antithrombin α form. The number of bound sialic acids of this solution was measured in the same manner as in Example 1. As a result, the number of bound sialic acids was 6.9 mol/mol and the binding ratio of sialic acid was 86%.

Example 16

Example of Purification of Protein S by Combination of Mixed Mode Carrier and Other Chromatography The CHO cell culture supernatant containing 102.1 mg of Protein S (pH was adjusted to 5.0 and precipitates were removed by centrifugation) was directly passed through the mixed mode column (manufactured by GE Healthcare, Capto MMC, column volume: 15.7 mL) equilibrated with buffer PQ (50 mmol/L acetic acid solution, pH 5.0) to adsorb Protein S thereto.

The column was washed with 78.5 mL of buffer PQ (50 mmol/L acetic acid solution, pH 5.0), and 157 mL of buffer PR (100 mmol/L sodium phosphate solution, pH 7.0) was applied to elute Protein S, and 242.2 mL of Protein S-containing aqueous solution was recovered. The recovery of Protein S in this process was as good as 89.5%.

A glycine solution was added to the aqueous solution containing Protein S recovered in the above mentioned process at a final concentration of 1.0 mol/L, followed by gently stirring. This solution was passed through the column (manufactured by GE Healthcare, Q Sepharose High Performance, column volume: 17.7 mL) equilibrated with buffer PS (10 mmol/L Tris buffer, pH 7.0) to adsorb Protein S thereto.

The column was washed with 88.5 mL of buffer PS (10 mmol/L Tris buffer, pH 7.0), and then 354 mL of buffer PT (10 mmol/L Tris buffer, 0.5 mol/L NaCl solution, pH 7.0) was applied to elute Protein S. 26.17 mL of Protein S-containing aqueous solution was recovered.

A glycine solution was added to the aqueous solution containing Protein S recovered in the above mentioned process at a final concentration of 1.0 mol/L, followed by gently stirring. This solution was passed through the column (manufactured by Bio-Rad, CHT ceramic hydroxyapatite Type I, column volume: 17.7 mL) equilibrated with buffer PU (10 mmol/L sodium phosphate buffer, pH 6.8) to adsorb Protein S thereto.

The column was washed with 88.5 mL of buffer PU (10 mmol/L sodium phosphate buffer, pH 6.8), and then 354 mL of buffer PV (400 mmol/L sodium phosphate buffer, pH 6.8) was applied to elute Protein S. 44.29 mL of Protein S-containing aqueous solution was recovered.

The aqueous solution containing Protein S recovered in the above mentioned process was concentrated by the ultrafiltration membrane (manufactured by Merck, a molecular weight cut off: 30 kilodaltons) to a proper concentration, followed by the exchange with buffer PW (20 mmol/L Tris buffer, 100 mmol/L sodium chloride, 1 mmol/L calcium chloride solution, pH 7.4). The purification yield in this purification process was 30.8%.

Figure 11:
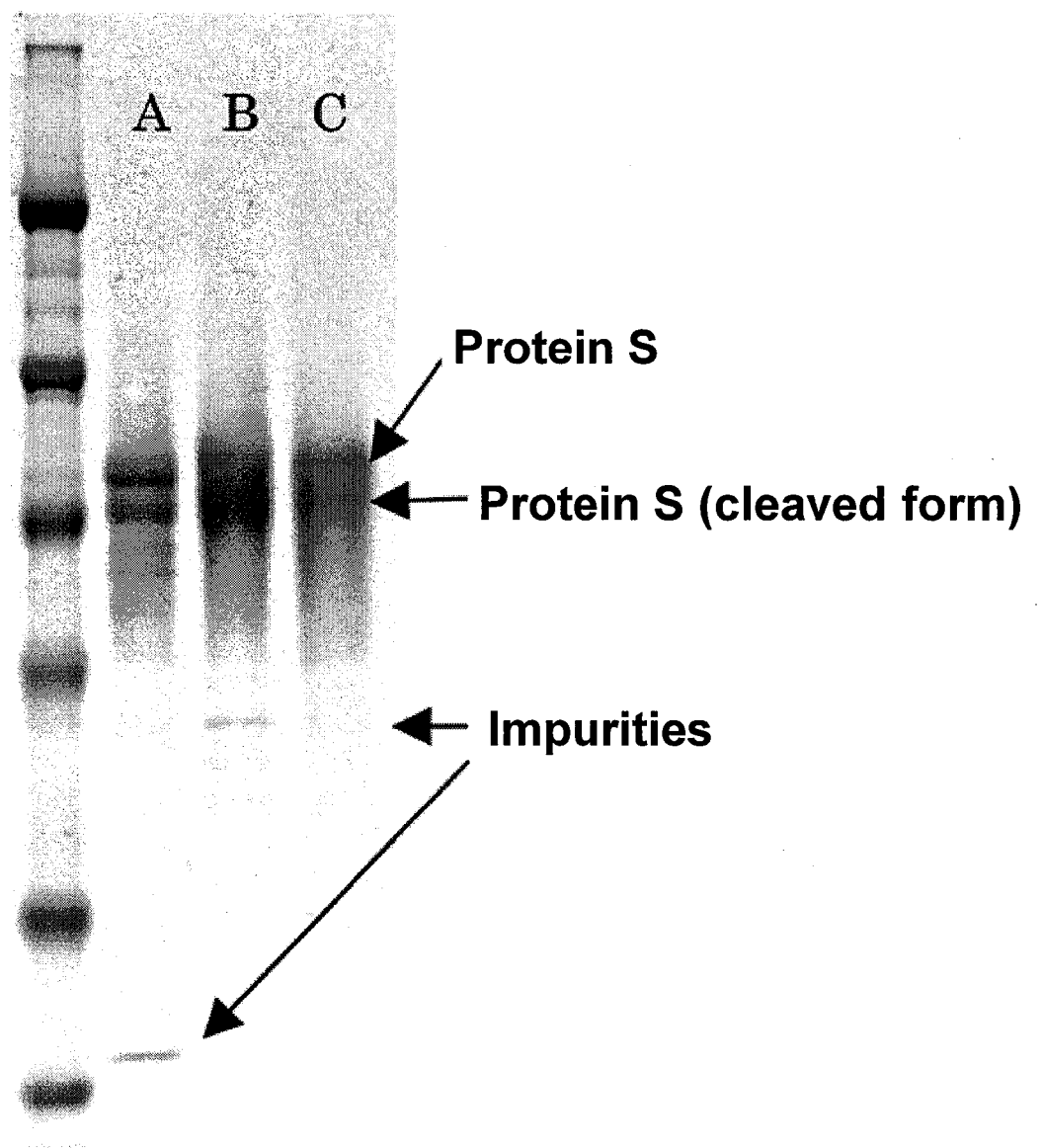
FIG. 11 shows the results of SDS-PAGE analysis of Protein S purified using the mixed mode carrier and Protein S purified without using the mixed mode carrier, in which A represents commercial Protein S (manufactured by Enzyme Research Laboratories), B represents Protein S obtained in Comparative Example 3 (purified without using the mixed mode carrier), and C represents Protein S obtained in Example 16 (purified using the mixed mode carrier).

The Protein S obtained by the method described in Example 16 (hereinafter, referred to as Protein S-Example 16) and the Protein S obtained by the method described in Comparative Example 3 (hereinafter, referred to as Protein S-Comparative Example 3) were analyzed by SDS-PAGE method (4-20% Tris-Glycine Gel, manufactured by Invitrogen, loading amount of protein of Protein S: 2.4 µg), and the results are shown in FIG. 11.

As shown in FIG. 11, the content of impurities was low in Protein S-Example 16.

The Protein S-Example 16 and the Protein S-Comparative Example 3 were held at 37° C. for 3 days, or they were also frozen at −20° C., respectively. Each sample was analyzed by SDS-PAGE method (4-20% Tris-Glycine Gel, manufactured by Invitrogen, loading amount of protein of Protein S: 2.4 µg) and the results are shown in FIG. 12.

Figure 12:
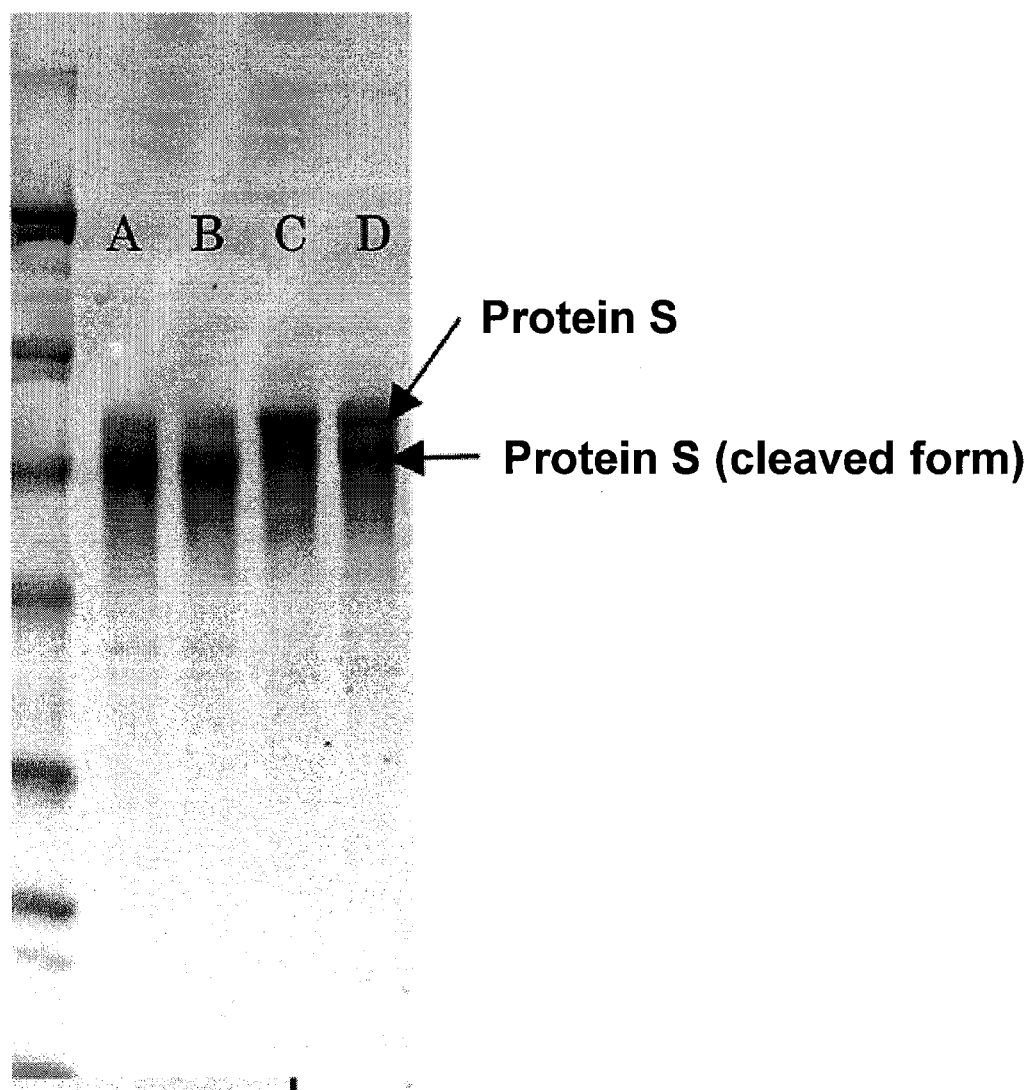
FIG. 12 shows the results of SDS-PAGE analysis of Protein S purified using the mixed mode carrier and Protein S purified without using the mixed mode carrier, in which A represents Protein S obtained in Comparative Example 3 (purified without using the mixed mode carrier), B represents Protein S obtained in Comparative Example 3 (purified without using the mixed mode carrier) and then held at 37° C. for 3 days, C represents Protein S obtained in Example 16 (purified using the mixed mode carrier), and D represents Protein S obtained in Example 16 (purified using the mixed mode carrier) and then held at 37° C. for 3 days.

As shown in FIG. 12, there was no change in the Protein S-Example 16 whereas the cleaved form was increased in the Protein S-Comparative Example 3. Therefore, it can be seen that a purification system by the mixed mode carrier and amino acids is used to improve purity of Protein S and to effectively remove protease causing the increase of the cleaved form.

Comparative Example 1

Example of Showing that Neuraminidase Cannot be Separated in Purification of the Antithrombin Culture Supernatant by the Typical Method by the Mixed Mode Carrier A CHO cell culture supernatant containing about 380 mg of Antithrombin was passed through the mixed mode column (manufactured by GE Healthcare, Capto adhere, column volume: 38 mL) equilibrated with buffer AJ (100 mmol/L sodium chloride, 20 mmol/L sodium phosphate buffer, pH 7.0) to adsorb Antithrombin.

The column was washed with 195 mL of buffer AJ (100 mmol/L sodium chloride, 20 mmol/L sodium phosphate buffer, pH 7.0), and then 152 mL of buffer AB (350 mmol/L sodium chloride, 20 mmol/L sodium phosphate buffer, pH 7.0) was applied to elute Antithrombin.

The Antithrombin concentration and the neuraminidase activity in the washing fraction before elution and in the eluate were measured in the same manner as in Example 1. The results are shown in Table 4.

TABLE 4

Separation of Antithrombin and neuraminidase by mixed mode chromatography in Comparative Example 1

|  | Antithrombin concentration (g/L) | Neuraminidase activity (U/L) |
| --- | --- | --- |
| Washing fraction before elution | Not detected | Not detected |
| Eluate | 2.56 | 20.3 |

As shown in Table 4, both Antithrombin and neuraminidase were detected in the eluate. Even though washing was performed before elution, Antithrombin and neuraminidase could not be separated by this purification method.

Comparative Example 2

Example of Showing that Quality of Antithrombin α Form is Affected by Non-Amino Acid Added Chromatography of the Concentrated-Diluted Culture Fluid The CHO cell culture supernatant containing about 35.3 g of Antithrombin was concentrated about 10-fold by an ultrafiltration membrane (manufactured by Merck Millipore, a molecular weight cut off: 30 kilodaltons). The concentrate from the above mentioned process was mixed with TritonX-100 and tributyl phosphate at their concentrations of 1% and 0.3%, respectively, followed by gently stirring.

This aqueous solution containing Antithrombin recovered from above mentioned process was diluted several-fold with purified water, and it was passed through the column (manufactured by GE Healthcare, Q Sepharose Fast Flow, column volume: 404 mL) equilibrated with buffer AK (20 mmol/L sodium phosphate buffer, pH 7.4) to adsorb Antithrombin.

The column was washed with 5 column volumes of buffer AK (20 mmol/L sodium phosphate buffer, pH 7.4), and then 6 column volumes of buffer AL (160 mmol/L sodium chloride, 20 mmol/L sodium phosphate buffer, pH 7.4) was applied to elute Antithrombin.

Sodium phosphate buffer was added to the aqueous solution containing Antithrombin recovered from the above mentioned process, and thus pH and conductivity were adjusted to 6.0 and 7 mS/cm, respectively. This solution was passed through the column (manufactured by JNC, Cellufine Sulfate, column volume: 608 mL) equilibrated with buffer AM (20 mmol/L sodium phosphate buffer, pH 6.0) to adsorb Antithrombin.

The column was washed with 5 column volumes of buffer AM (20 mmol/L sodium phosphate buffer, pH 6.0), and then Antithrombin was eluted with a linear gradient of sodium chloride by buffer AM (20 mmol/L sodium phosphate buffer, pH 6.0) and buffer AN (1 mol/L sodium chloride, 20 mmol/L sodium phosphate buffer, pH 6.0), and the recovered liquid was neutralized.

The aqueous solution containing Antithrombin thus recovered from the above mentioned process was concentrated about more than 10-fold by an ultrafiltration membrane (manufactured by Merck Millipore, a molecular weight cut off: 30 kilodaltons), and precipitates were filtered.

Buffer AO (3 mol/L ammonium sulfate, 20 mmol/L sodium phosphate buffer, pH 6.8) was added to the aqueous solution containing Antithrombin recovered from the above mentioned process for several-fold dilution. This solution was passed through the column (manufactured by GE Healthcare, Phenyl Sepharose 6 Fast Flow, column volume: 304 mL) equilibrated with buffer AP (2 mol/L ammonium sulfate, 20 mmol/L sodium phosphate buffer, pH 6.8) to adsorb Antithrombin.

The column was washed with 3 column volumes of buffer AP (2 mol/L ammonium sulfate, 20 mmol/L sodium phosphate buffer, pH 6.8), and then Antithrombin was eluted with a linear gradient of sodium sulfate.

The aqueous solution containing Antithrombin α form recovered from the above mentioned process was concentrated by the ultrafiltration membrane (a molecular weight cut off: 10 kilodaltons) to a proper concentration, and then exchanged with buffer AQ (20 mmol/L sodium citrate buffer, pH 7.0). This solution was used as a final purification product.

The number of bound sialic acids of Antithrombin α form contained in the final purification product was measured in the same manner as in Example 1. The number of bound sialic acids was low compared to that of Example 4, and was lowered to 4.5 mol/mol (binding ratio: 56%).

As described above, when the anion exchange carrier is used in the first purification step, it is required to concentrate and dilute the culture supernatant. When the culture supernatant was concentrated, neuraminidase contained in the culture supernatant was also concentrated and cause cleavage of sialic acid of Antithrombin by its activity, then the number of bound sialic acids of the purification sample was reduced.

Therefore, even though the protein composition is directly purified by the anion exchange carrier in the first purification step, it is difficult to purify Antithrombin while maintaining its quality.

Comparative Example 3

Example of Showing that Yield is Low and Protease Causing Increase of Cleaved Form Cannot be Removed when No Mixed Mode Carrier is Used in Purification of the Culture Supernatant Containing Protein S The CHO cell culture supernatant containing 16.1 g of Protein S was concentrated using the ultrafiltration membrane (manufactured by Merck, a molecular weight cut off: 10 kilodaltons). The buffer was exchanged with buffer PX (20 mmol/L Tris buffer, 120 mmol/L NaCl, pH 7.4) and the concentrate was diluted 2-fold at the same time. The solution thus prepared was directly passed through the anion exchange column (manufactured by GE Healthcare, Q Sepharose Fast Flow, column volume: 589 mL) equilibrated with buffer PY (20 mmol/L Tris buffer, 150 mmol/L NaCl, pH 7.4) to adsorb Protein S thereto.

The column was washed with 5.9 L of buffer PY (20 mmol/L Tris buffer, 150 mmol/L NaCl, pH 7.4), and then 1.8 L of buffer PZ (20 mmol/L Tris buffer, pH 7.4) was applied to further wash the column.

Thereafter, Protein S was eluted with 5.9 L of buffer Pa (20 mmol/L Tris buffer, 150 mmol/L NaCl, 25 mmol/L $CaCl_2$, pH 7.4) to recover an aqueous solution containing Protein S.

About 6-fold concentration of the aqueous solution containing Protein S thus recovered in the above mentioned process was performed by an ultrafiltration membrane (manufactured by Merck, a molecular weight cut off: 10 kilodaltons), and then the buffer was exchanged with buffer PY. The solution thus prepared was directly passed through to the anion exchange column (manufactured by GE Healthcare, Q Sepharose Fast Flow, column volume: 393 mL) equilibrated with buffer PY. The column was washed with 2.0 L of buffer Pb (20 mmol/L Tris buffer, 200 mmol/L NaCl, pH 7.4), and then 3.9 L of buffer Pc (20 mmol/L Tris buffer, 500 mmol/L NaCl, pH 7.4) was used for elution to recover an aqueous solution containing Protein S.

The aqueous solution containing Protein S thus recovered in the above mentioned process was directly passed through the column (manufactured by Bio-Rad, Macro Prep Ceramic hydroxyapatite, column volume: 589 mL) equilibrated with buffer PU (10 mmol/L sodium phosphate buffer, pH 6.8) to adsorb Protein S thereto. The column was washed with 2.9 L of buffer PU (10 mmol/L sodium phosphate buffer, pH 6.8), and then Protein S was eluted with buffer Pd (500 mmol/L sodium phosphate buffer, pH 6.8) to recover an aqueous solution containing Protein S.

The aqueous solution containing Protein S thus recovered in the above mentioned process was further purified by a column (manufactured by Bio-Rad, Macro Prep Ceramic hydroxyapatite) with a column volume of 196 mL in the same manner as in the above mentioned process.

The solution containing Protein S thus obtained in the above mentioned process was filtered by Planova 20N (manufactured by Asahi Kasei Medical), and then concentrated by the ultrafiltration membrane (manufactured by Merck, a molecular weight cut off: 10 kilodaltons). The buffer was exchanged with buffer PW (20 mmol/L Tris buffer, 100 mmol/L sodium chloride, 1 mmol/L calcium chloride solution, pH 7.4). The purification yield of this purification process was 3.7%, which was about ¹⁄₁₀ of Example 14.

Although the present invention has been described in connection with the exemplary embodiments in detail, it will be apparent to those skilled in the art that various modifications and changes may be made thereto without departing from the scope and spirit of the invention.

Although the present invention has been described in connection with the specific embodiments in detail, it will be apparent to those skilled in the art that various modifications and changes may be made thereto without departing from the intention and scope of the invention. Meanwhile, this application is based on U.S. Provisional Application No. 61/502,426 filed on Jun. 29, 2011, the entire contents of which are incorporated hereinto by reference.

INDUSTRIAL APPLICABILITY

According to the present invention, impurities can be rapidly removed from a protein composition and an objective protein can be effectively recovered.

The invention claimed is:

1. A method for purifying antithrombin, comprising a first chromatographic process including the following processes of (a) to (c):
   (a) a process of contacting a composition comprising the antithrombin and impurities comprising sialidase with an anion exchange carrier so that the antithrombin and the impurities are adsorbed to the anion exchange carrier;

(b) a process of washing the anion exchange carrier to which the antithrombin and the impurities are adsorbed using a first buffer weakening affinity of the impurities for the anion exchange carrier so as to remove the impurities and to inhibit the degradation of sialic acids by inhibiting the activity of sialidase, said first buffer containing 0.1 to 1 mol/L of glycine so as to remove the impurities, and said first buffer being one or more selected from the group consisting of phosphate, citrate, acetate, succinate, maleate, borate, Tris, HEPES, MES, PIPES, MOPS, TES, and Tricine; and (c) a process of eluting the antithrombin from the anion exchange carrier by using a second buffer which is one or more selected from the group consisting of phosphate, citrate, acetate, succinate, maleate, borate, Tris, HEPES, MES, PIPES, MOPS, TES, and Tricine so as to purify antithrombin in which the number of bound sialic acids is 70% or more of the maximum number to be added, wherein the maximum number to be added is 8 mol/mol for Antithrombin α form or 6 mol/mol for Antithrombin β form.

2. The purification method according to claim 1, wherein a recovery of the purified antithrombin is 50% or more.

3. The purification method according to claim 1, further comprising one or more chromatographic processes after the first chromatographic process.

4. The purification method according to claim 1, which further comprises a second chromatographic process, said second chromatographic process using any one selected from the group consisting of a mixed mode carrier, an anion exchange carrier, an anion exchange membrane, a cation exchange carrier, a cation exchange membrane, a hydrophobic interaction carrier, a size exclusion carrier, a gel filtration carrier, a reversed-phase carrier, a hydroxyapatite carrier, a fluorapatite carrier, a sulfated cellulose carrier, and a sulfated agarose carrier.

5. The purification method according to claim 1, wherein the amount of glycine is 0.3-1 mol/L.

* * * * *